(12) United States Patent
Rodriguez et al.

(10) Patent No.: US 8,993,626 B2
(45) Date of Patent: Mar. 31, 2015

(54) METHODS OF TREATMENT USING STERCULIC ACID

(75) Inventors: Ignacio R. Rodriguez, Derwood, MD (US); Jiahn-Dar Huang, Rockville, MD (US); Juan A. Amaral, Silver Spring, MD (US); Jung Wha Lee, Gaithersburg, MD (US); William Samuel, Gaithersburg, MD (US); Ignacio Marcos Larrayoz, Sarriguren (ES)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 0 days.

(21) Appl. No.: 13/805,429

(22) PCT Filed: Jun. 24, 2011

(86) PCT No.: PCT/US2011/041766
§ 371 (c)(1),
(2), (4) Date: Feb. 19, 2013

(87) PCT Pub. No.: WO2011/163560
PCT Pub. Date: Dec. 29, 2011

(65) Prior Publication Data
US 2013/0143966 A1 Jun. 6, 2013

Related U.S. Application Data

(60) Provisional application No. 61/358,485, filed on Jun. 25, 2010.

(51) Int. Cl.
*A61K 31/201* (2006.01)

(52) U.S. Cl.
CPC .................................. *A61K 31/201* (2013.01)
USPC ........................................................ 514/559

(58) Field of Classification Search
CPC .................................................. A61K 31/201
USPC ........................................................ 514/559
See application file for complete search history.

(56) References Cited

U.S. PATENT DOCUMENTS

| | | |
|---|---|---|
| 4,014,335 A | 3/1977 | Arnold et al. |
| 4,287,175 A | 9/1981 | Katz et al. |
| 4,343,787 A | 8/1982 | Katz et al. |
| 4,778,630 A | 10/1988 | Moreton et al. |
| 5,466,233 A | 11/1995 | Weiner et al. |
| 5,518,732 A | 5/1996 | Nigam et al. |
| 5,707,643 A | 1/1998 | Ogura et al. |
| 5,718,922 A | 2/1998 | Herrero-Vanrell et al. |
| 5,869,079 A | 2/1999 | Wong et al. |
| 5,902,598 A | 5/1999 | Chen et al. |
| 6,154,671 A | 11/2000 | Parel et al. |
| 6,251,090 B1 | 6/2001 | Avery et al. |
| 6,331,313 B1 | 12/2001 | Wong et al. |
| 6,375,972 B1 | 4/2002 | Guo et al. |
| 6,410,045 B1 | 6/2002 | Schultz et al. |
| 7,524,490 B2 * | 4/2009 | Geng ........................... 424/93.1 |
| 2003/0157552 A1 * | 8/2003 | Hayden et al. ................. 435/7.1 |
| 2007/0219211 A1 | 9/2007 | Kamboj et al. |

FOREIGN PATENT DOCUMENTS

EP 0238198 9/1987

OTHER PUBLICATIONS

Soulard et al. Development of a high-throughput screening assay for stearoyl-CoA desaturase using rat liver microsomes, deuterium labled steroyl-CoA and mass spectrometry. Analytica Chimca Acta, Oct. 3, 2008, vol. 627, No. 1, pp. 105-111 abstract.*
A Randomized, Placebo-Controlled, Clinical Trial of High-Dose Supplementation with Vitamins C and E., Beta Carotene, and Zinc for Age-Related Macular Degeneration and Vision Loss, Age-Related Eye Disease Study Research Group (AREDS Report No. 8), Arch. Ophthalmol., 2001, 119, 1417-1436.
Bao et al., "Carbocyclic Fatty Acids in Plants: Biochemical and Molecular Genetic Characterization of Cyclopropane Fatty Acid Synthesis of Sterculiafoetida", PNAS, 2002, 99(10), 7172-7177.
Bousserouel et al., "Different Effects of N-6 and N-3 Polyunsaturated Fatty Acids on the Activation of Rat Smooth Muscle Cells by Interleukin-1 Beta", J. Lipid Res., 2003, 44, 601-611.
Brown et al., "7-Hydroperoxycholesterol and Its Products in Oxidized Low Density Lipoprotein and Human Atherosclerotic Plaque", J. Lipid. Res., 1997, 38, 1730-1745.
Calder, "N-3 Polyunsaturated Fatty Acids, Inflammation, and Inflammatory Diseases1-3", Am J Clin Nutr., 2006, 83(Suppl), 1505S-1519S.
Campos et al., "A Novel Imaging Technique for Experimental Choroidal Neovascularization", Invest. Ophthalmol. Vis. Sci., 2006, 47, 5163-5170.
Chen et al, "EPA and DHA Attenuate Ox-LDL-Induced Expression of Adhesion Molecules in Human Coronary Artery Endothelial Cells Via Protein Kinase B Pathway", J. Mol. Cell. Cardiol., 2003, 35, 769-775.
Curcio et al., "Aging, Age-Related Macular Degeneration, and the Response-to-Retention of Apolipoprotein B-Containing Lipoproteins", Progress Retin. Eye Res., 2009, 28, 393-422.
Dobi et al., "A New Model of Experimental Choroidal Neovascularization in the Rat", Arch Ophthalmol., 1989, 107, 264-269.
Dobrzyn et al., "Stearoyl-CoA Desaturase-1 Deficiency Reduces Ceramide Synthesis by Downregulating Serine Palmitoyltransferase and Increasing Beta-Oxidation in Skeletal Muscle", Am J Physiol Endocrinol Metab, 2005, 288, E599-E607.

(Continued)

*Primary Examiner* — Jennifer M Kim

(57) ABSTRACT

The use of sterculic acid, and the pharmaceutically acceptable salt forms thereof, described for the treatment of inflammation, in particular, 7-ketocholesterol induced inflammation, 7-ketocholesterol toxicity, and unregulated angiogenesis.

10 Claims, 20 Drawing Sheets

(56) References Cited

OTHER PUBLICATIONS

Doshi et al., "Effect of Dietary Enrichment with n-3 Polyunsaturated Fatty Acids (PUFA) or n-9 PUFA on Arachidonate Metabolism In Vivo and Experimentally Induced Inflammation in Mice", Biol Pharm Bull., 2004, 27(3), 319-323.

Dulakk et al., "Vascular Endothelial Growth Factor Synthesis in Vascular Smooth Muscle Cells Is Enhanced by 7-Ketocholesterol and Lysophosphatidylcholine Independently of Their Effect on Nitric Oxide Generation", Athero, 2001, 159, 325-332.

Duran et al., "7-ketocholesterol inhibits Na,K-ATPase activity by decreasing expression of its alphal-subunit and membrane fluidity in human endothelial cells", Cell Mol Biol (Noisy-le-grand), 2010, 56 Suppl, OL1434-OL1441.

Enoch et al., "Mechanism of Rat Liver Microsomal Stearyl-CoA Desaturase. Studies of the Substrate Specificity, Enzyme-Substrate Interactions, and the Function of Lipid", J Biol Chem., 1976, 251(16), 5095-5103.

Fermor et al., "Fatty Acid Composition of Normal and Malignant Cells and Cytotoxicity of Stearic, Oleic and Sterculic Acids In Vitro", Eur J Cancer., 1992, 28A(6-7),1143-1147.

Garcia-Cruset et al., "Oxysterol profiles of Normal Human Arteries, Fatty Streaks and Advanced Lesions", Free Radic Res., 2001, 35(1), 31-41.

Gilmore, "Introduction to NF-kappaB: Players, Pathways, Perspectives", Oncogene, 2006, 25, 6680-6684.

Gomez et al., "Effects of Sterculic Acid on Stearoyl-CoA Desaturase in Differentiating 3T3-Li Adipocytes", Biochem Biophys Res Commun., 2003, 300, 316-326.

Guyton et al., "Development of the Lipid-Rich Core in Human Atherosclerosis,", Arterio Thromb Vasc Biol., 1996, 16, 4-11.

Harris et al., "Effects of Fish Oil on VLDL Triglyceride Kinetics in Humans", J Lipid Res., 1990, 31, 1549-1558.

Harvey et al., "Long-Chain Saturated Fatty Acids Induce Pro-Inflammatory Responses and Impact Endothelial Cell Growth", Clin Nutr., 2010, 29, 492-500.

He et al., "Associations of Dietary Long-Chain n-3 Polyunsaturated Fatty Acids and Fish with Biomarkers of Inflammation and Endothelial Activation (from the Multi-Ethnic Study of Atherosclerosis [MESA])", Am J Cardiol., 2009, 103(9), 1238-1243.

Hughes et al., "Cytotoxicity of Oxidized LDL to Porcine Aortic Smooth Muscle Cells is Associated with the Oxysterols 7-Ketocholesterol and 7-Hydroxycholesterol", Arterioscler Thromb., 1994, 14,1177-1185.

James et al., "The Inhibition of Unsaturated Fatty Acid Biosynthesis in Plants by Sterculic Acid", Eur J Biochem., 1968, 3, 318-325.

Jeffcoat et al., "Studies on the Inhibition of the Desaturases by Cyclopropenoid Fatty Acids", Lipids., 1977,12(6), 480-485.

Jialal et al., "The Role of Oxidized Low Density Lipoprotein in Atherogenesis", J Nutr., 1996, 126(Suppl),1053S-1057S.

Kamei et al., "Scavenger Receptors for Oxidized Lipoprotein in Age-Related Macular Degeneration", Invest Ophthalmol Vis Sci., 2007, 48, 1801-1807.

Khoo et al., "Manipulation of Body Fat Composition With Sterculic Acid Can Inhibit Mammary Carcinomas In Vivo", Br J Cancer., 1991, 63, 97-101.

Kita et al., "The Role of Oxidized Low Density Lipoprotein in the Pathogenesis of Atherosclerosis", Eur Heart J., 1990, 11(Suppl E), 122-127.

Koto et al., "Eicosapentaenoic Acid is Anti-Inflammatory in Preventing Choroidal Neovascularization in Mice", Invest Ophthalmol Vis Sci., 2007, 48, 4328-4334.

Larrayoz et al., "7-Ketocholesterol-Induced Inflammation: Involvement of Multiple Kinase Signaling Pathways Via NfKb but Independently of Reactive Oxygen Species Formation", Invest Ophthalmol Vis Sci., 2010, 51, 4942-4955.

Leonarduzzi et al., "Up-Regulation of the Fibrogenic Cytokine TGF-beta1 by Oxysterols: A Mechanistic Link Between Cholesterol and Atherosclerosis", FASEB J., 2001, 15(9), 1619-1621.

Li et al., "NADPH Oxidase Links Endoplasmic Reticulum Stress, Oxidative Stress, and PKR Activation to Induce Apoptosis", J Cell Biol., 2010, 191(6), 1113-1125.

Li et al., "NF-kappaB Regulation in the Immune System", Nat Rev Immunol., 2002, 2, 725-734.

Lizard et al., "Induction of Apoptosis and of Interleukin-1beta Secretion by 7beta-Hydroxycholesterol and 7-Ketocholesterol: Partial Inhibition by Bcl-2 Overexpression", FEBS Letters, 1997, 419, 276-280.

Luthra et al., "7-Ketocholesterol Activates Caspases-3/7, -8, and -12 in Human Microvascular Endothelial Cells In Vitro", Microvasc Res., 2008, 75, 343-350.

Matsuura et al., "Oxidative Modification of Low-Density Lipoprotein and Immune Regulation of Atherosclerosis", Progress Lipid Res., 2006, 45, 466-486.

Miguet et al., "Ceramide Generation Occurring During 7beta-Hydroxycholesterol- and 7-Ketocholesterol-Induced Apoptosis Is Caspase Independent and is Not Required to Trigger Cell Death", Cell Death Differ, 2001, 8, 83-99.

Moreira et al., "7-Ketocholesterol is Present in Lipid Deposits in the Primate Retina: Potential Implication in the Induction of VEGF and CNV Formation", Invest Ophthalmol Vis Sci., 2009, 50, 523-532.

Moritera et al., "Microspheres of Biodegradable Polymers as a Drug-Delivery System in the Vitreous", Invest Ophthalmol Vis Sci., 1991, 32(6), 1785-1790.

Nishio et al., "Oxidized LDL Induces Apoptosis in Cultured Smooth Muscle Cells: A Possible Role for 7-Ketocholesterol", Biochem Biophys Res Commun., 1996, 223, 413-418.

Ntambi, "Regulation of Stearoyl-CoA Desaturase by Polyunsaturated Fatty Acids and Cholesterol", J Lipid Res., 1999, 40, 1549-1558.

Pahl et al., "Activators and Target Genes of Rel/NF-kappaB Transcription Factors", Oncogene, 1999, 18, 6853-6866.

Psota et al., "Dietary Omega-3 Fatty Acid Intake and Cardiovascular Risk", Am J Cardiol., 2006, 98(Suppl), 3i-18i.

Ramsden et al, "N-6 Fatty Acid-Specific and Mixed Polyunsaturate Dietary Interventions Have Different Effects on CHD Risk: A Meta-Analysis of Randomised Controlled Trials", Br J Nutr., 2010, 104, 1586-1600.

Rodriguez et al., "Cytotoxicity of Oxidized Low-Density Lipoprotein in Cultured Rpe Cells is Dependent on the Formation of 7-Ketocholesterol", Invest Ophthalmol Vis Sci., 2004, 45, 2830-2837.

Rodriguez et al., "Photodamage Generates 7-Keto- and 7-Hydroxycholesterol in the Rat Retina Via a Free Radical-Mediated Mechanism", Photochem Photobiol., 2009, 85(5),1116-1125.

Rodriguez et al., "Cholesterol Oxidation in the Retina: Implications of 7KCh Formation in Chronic Inflammation and Age-Related Macular Degeneration", J Lipid Res., 2010, 51, 2847-2862.

SanGiovanni et al., "The Relationship of Dietary Omega-3 Long-Chain Polyunsaturated Fatty Acid Intake with Incident Age-Related Macular Degeneration, Age-Related Eye Disease Study Research Group, AREDS Report No. 23", Arch Ophthalmol., 2008, 126(9), 1274-1279.

Sevitt et al. "Platelets and Foam Cells in the Evolution of Atherosclerosis, Histological and Immunohistological Studies of Human Lesions", Atherosclerosis, 1986, 61, 107-115.

Sottero et al., "Cholesterol Oxidation Products and Disease: An Emerging Topic of Interest in Medicinal Chemistry", Curr Med Chem., 2009, 16, 685-705.

Tull et al., "Omega-3 Fatty Acids and Inflammation: Novel Interactions Reveal a New Step in Neutrophil Recruitment", PLoS Biol., 2009, 7(8), 11 pages.

Vallabhapurapu et al., "Regulation and Function of NF-kappaB Transcription Factors in the Immune System", Annu Rev Immunol., 2009, 27, 693-733.

Velasco et al., "Up-Regulation of IkappaBbeta and Abrogation of NF-kappaB Activity in Peritoneal Macrophages Stimulated with Lipopolysaccharide", J Biol Chem., 1997, 272(37), 23025-23030.

(56) References Cited

OTHER PUBLICATIONS

Wajant et al., "Tumor Necrosis Factor Signaling", Cell Death Differ., 2003, 10, 45-65.

Xing et al., "Dynamic Monitoring of Cytotoxicity on Microelectronic Sensors", Chemical Research in Toxicology, 2005, 18, 154-161.

Yamada et al., "Oxidized Low Density Lipoproteins Induce a Pathologic Response by Retinal Pigmented Epithelial Cells", J Neurochem., 2008, 105, 1187-1197.

Zoeller et al., "The Importance of the Stearoyl-CoA Desaturase System in Octadecenoate Metabolism in the Morris Hepatoma 7288C", Biochim Biophys Acta., 1985, 845(3), 380-388.

\* cited by examiner

Sterculic acid
1 mM/drop

Oleic acid
1 mM/drop

Phase-contrast images of ARPE19 cells at 24 hr after sterculic acid treatment in the presence of 7KCh.

METHODS OF TREATMENT USING STERCULIC ACID

CROSS-REFERENCE TO RELATED APPLICATIONS

This application is the national stage of PCT/US2011/041766, filed Jun. 24, 2011, which claims the benefit of priority to U.S. Provisional Application No. 61/358,485, filed Jun. 25, 2010, the disclosures of which are incorporated herein by reference in their entireties.

TECHNICAL FIELD

The present invention is directed to sterculic acid, and its derivatives, for the treatment of diseases mediated by, for example, 7-ketocholesterol-induced inflammation and angiogenesis.

BACKGROUND

Sterculic acid, 8-(2-octacyclopropen-1-yl)octanoic acid:

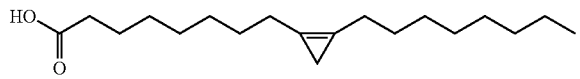 [SMILES: CCCCCCCCC1=C(CCCCCCCC(=O)O)C1]

is a naturally occurring cyclopropene acid present in kapok seed oil, cottonseed oil, and in the seeds of the *Sterculia foetida* tree. Sterculic acid has been reported to be a non-specific inhibitor of stearoyl-Co desaturase (SCD), which has been implicated in several disease states, including cardiovascular disease, obesity, non-insulin-dependent diabetes mellitus, skin disease, hypertension, neurological diseases, immune disorders and cancer. Ntambi, *J. Lipid Res.*, 1990, 40, 1549-1558. Sterculic acid, however, has not been found to be useful in vivo because at physiological doses, it is not selective for SCD and inhibits other desaturases. See U.S. Published Application 2007/0219211 at [0006].

Sterculic acid's ability to increase the stearic:oleic acid ratio has led to suggestions that sterculic acid might inhibit tumor growth. But while some researchers have reported that sterculic acid can inhibit malignant cell growth in vitro, others have reported that sterculic acid is actually a promoter of 2' acetoaminofluorene-induced liver carcinogenesis and that when applied to hepatoma cells, inhibition of doubling time was observed. Khoo, et al. Manipulation of body fat composition with sterculic acid can inhibit mammary carcinomas in vivo, *Br. J. Cancer* (1991), 63, 97-101.

7-Ketocholesterol (7KCh) is a major oxidation product of cholesterol and is found in atherosclerotic plaques. Accumulation of 7-ketocholesterol in lipoprotein deposits is suspected of causing macrophage foam cell formation resulting in atheromatous plaques. In addition to a role in atherosclerosis, 7-ketocholesterol cytotoxicity has been implicated in the pathogenesis of Alzheimer's disease, age-related macular degeneration, and some forms of cancer. To date, no compounds have been demonstrated to inhibit 7-ketocholesterol-mediated inflammation and cytotoxicity. As a result, treatments for diseases associated with 7-ketocholesterol accumulation are needed.

Angiogenesis is the development of new blood vessels from preexisting ones and is an important natural process that occurs in the body, both in health and in disease. In physiological conditions such as pregnancy and wound healing, angiogenesis is tightly regulated. In pathological conditions, however, such as inflammatory diseases, tumor growth, and tumor metastasis, a chronic "unregulated" angiogenic state often exacerbates the disease. Excessive growth of blood vessels or neovascularization has been shown to be a causative factor in many diseases such as cancer and diabetic retinopathy. Anti-angiogenic therapies aimed at halting new blood vessel growth is an active field of research.

Wet age-related macular degeneration (wet AMD) is an example of a disease state characterized by abnormal blood vessel formation (angiogenesis) under the retina and macula. These new blood vessels may bleed and leak fluid, causing the macula to bulge, distorting or destroying vision in the affected eye. To date, very few treatments exist for the management of wet macular degeneration. Presently, patients receive repeated intravitreal injections of anti-VEGF antibodies directly into the eye. Such treatments are expensive and are stressful to the patient. Thus, new, less invasive treatments are needed to treat wet AMD.

SUMMARY

The present invention is directed to methods of using sterculic acid, or a pharmaceutically acceptable salt form thereof, for the treatment of inflammation, specifically, 7-ketocholesterol mediated inflammation, 7-ketocholesterol cytotoxicity, or unregulated angiogenesis.

DETAILED DESCRIPTION OF ILLUSTRATIVE EMBODIMENTS

Figure 1:
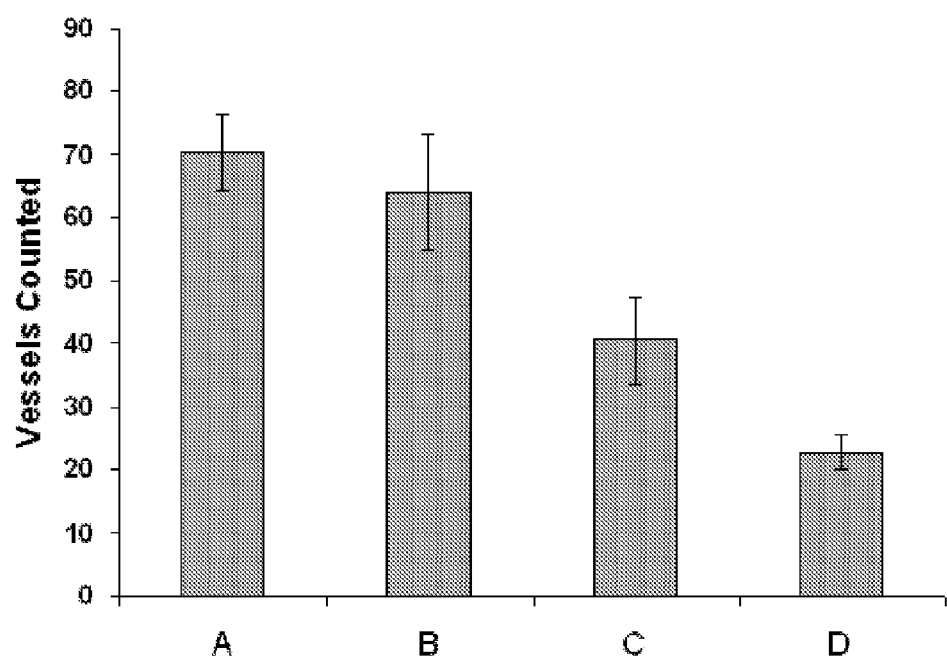
FIG. 1 depicts results from experiments demonstrating that sterculic acid inhibits bFGF-induced angiogenesis in chick embryos. Results shown are reported as the reduction in angiogenic stimulation (vessels counted) compared to untreated controls. A, bFGF (5 ng/ml); B, bFGF (5 ng/ml)+5 μl DMSO; C, bFGF (5 ng/ml)+5 μl DMSO containing 1 μg/ml sterculic acid; D, bFGF (5 ng/ml)+5 μl DMSO containing 10 μg/ml sterculic acid.

The present invention is directed to methods of using therapeutically effective amounts of sterculic acid, or a pharmaceutically acceptable salt thereof, for the treatment of inflammation, in particular, 7-ketocholesterol mediated inflammation, 7-ketocholesterol cytotoxicity, or unregulated angiogenesis. Diseases mediated by 7-ketocholesterol-induced inflammation and 7-ketocholesterol cytotoxicity are known in the art and include, for example, atherosclerosis age-related macular degeneration, and Alzheimer's disease. Diseases mediated by unregulated angiogenesis are also known in the art and include, for example, certain cancers and age-related macular degeneration.

Also within the scope of the invention are methods of treating artherosclerosis using sterculic acid or a pharmaceutically acceptable salt form thereof. It is also envisioned that sterculic acid or a pharmaceutically acceptable salt form thereof can be used in methods of treating Alzheimer's disease. It is further envisioned that sterculic acid or a pharmaceutically acceptable salt form thereof can be used in methods of treating age-related macular degeneration.

As used herein, "a pharmaceutically acceptable salt form" means any pharmaceutically acceptable salt of the compound of formula (I). Salts may be prepared from pharmaceutically acceptable acids and bases including inorganic and organic acids and bases. Preferred base salts include sodium, potassium, calcium, magnesium, and aluminum salts.

As used herein, "therapeutically effective amount" refers to the quantity of the compound that is sufficient to provide the desired therapeutic response.

Compositions

Sterculic acid, or a pharmaceutically acceptable salt form thereof, may be formulated into various pharmaceutical forms for administration purposes. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage, the therapeutically effective amount and frequency of administration depends on the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Ophthalmic Compositions

Sterculic acid, or a pharmaceutically acceptable salt form thereof, can be formulated into compositions for application to the eye of patients in need of therapy. Thus, such compositions are adapted for pharmaceutical use as an eye drop, peri- or intraocular injections, or in contact lenses, inserts or the like, as described in greater detail below. Accordingly, formulation of sterculic acid, or a pharmaceutically acceptable salt form thereof, into sterile water containing any desired diluents, salts, pH modifying materials, and the like as are known to persons skilled in the pharmaceutical formulations art may be performed in order to achieve a solution compatible with administration to the eye. It may be that eye drops, injections, inserts, contact lenses, gels and other topical liquid forms may require somewhat different formulations. All such formulations consistent with direct administration to the eye are comprehended hereby.

Antioxidants

The compositions of the invention may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities. As such, the amount of antioxidant(s) to be administered should be enough to be effective while not causing any untoward effect. Such doses may be adjusted by a physician as needed, within the maximum levels set by regulatory authorities, and is well within the purview of the skilled artisan to determine the proper and effective dose. Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-Acetylcysteine may be present in a range of about 0.1% to about 5.0% weight by volume. Ascorbic acid or salt may also be present in a range of about 0.1% to about 5.0% weight by volume. Other sulfhydryls, if included, may be the same range as for N-acetylcysteine. Other exemplary compounds include mercaptopropionyl glycine, N-acetyl cysteine, β-mercaptoethylamine, glutathione and similar species, although other anti-oxidant agents suitable for ocular administration, e.g., ascorbic acid and its salts or sulfite or sodium metabisulfite may also be employed.

Buffering Agents

A buffering agent may be used to maintain the pH of eye drop formulations in the range of about 4.0 to about 8.0; this is necessary to prevent corneal irritation. The buffer may be any weak acid and its conjugate base with a pKa of about 4.0 to about 5.5; e.g. acetic acid/sodium acetate; citric acid/sodium citrate. The pKa of the hydroxylamines is about 6.0. For direct intravitreal or intraocular injection, formulations should be at pH 7.2 to 7.5, preferably at pH 7.3-7.4.

Tonicity Agents

The compounds of the present invention may also include tonicity agents suitable for administration to the eye. Among those suitable is sodium chloride to make formulations of the present invention approximately isotonic with 0.9% saline solution.

Viscosity Enhancing Agents

In certain embodiments, the compounds of the invention are formulated with viscosity enhancing agents. Exemplary agents are hydroxyethylcellulose, hydroxypropylcellulose, methylcellulose, and polyvinylpyrrolidone. The viscosity agents may exists in the compounds up to about 2.0% weight by volume. It may be preferred that the agents are present in a range from about 0.2% to about 0.5% weight by volume. A preferred range for polyvinylpyrrolidone may be from about 0.1% to about 2.0% weight by volume. One skilled in the art may prefer any range established as acceptable by the Food and Drug Administration.

Co-Solvents

The compounds of the invention may have co-solvents added if needed. Suitable cosolvents may include glycerin, polyethylene glycol (PEG), polysorbate, propylene glycol, mannitol and polyvinyl alcohol. The presence of the co-solvents may exist in a range of about 0.2% to about 4.0% weight by volume. It may be preferred that mannitol may be formulated in the compounds of the invention in a range of about 0.5% to about 4.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, and from about 0.01% to about 0.2% weight by volume of methyl or propylparabens.

Co-Administration

In some embodiments of the invention, the compound(s) of the invention are administered with another compound known in the art that is useful for treating a disease or disorder that is the target of the compounds of the invention. Thus the composition of the invention may further contain at least one other compound known in the art for treating the disease or disorder to be treated. The other compound(s) known in the art may be administered simultaneously with the compound(s) of the invention, or may be administered sequentially. Similarly, the methods of the invention include using such combination therapy.

Delivery Methods

Compositions comprising the compounds of the invention may be delivered to the eye of a patient in one or more of several delivery modes known in the art. In a preferred embodiment, the compositions are topically delivered to the eye in eye drops or washes. In another embodiment, the compositions are delivered in a topical ophthalmic ointment. In another embodiment, the compositions may be delivered to various locations within the eye via periodic subconjunctival or intraocular injection, or by infusion in an irrigating solution such as BSS® or BSS PLUS® (Alcon USA, Fort Worth, Tex.) or by using pre-formulated solutions of the hydroxylamines in excipients such as BSS® or BSS PLUS®.

Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. A direct injection of drugs into the vitreous body used for treating diseases has been used, in which microspheres or liposomes were used to release drugs slowly (Moritera, T. et al. "Microspheres of biodegradable polymers as a drug-delivery system in the vitreous" *Invest. Ophthalmol. Vis. Sci.* 1991 32(6):1785-90).

Formulations for injection are preferably designed for single-use administration and do not contain preservatives. Injectable solutions should have isotonicity equivalent to 0.9% sodium chloride solution (osmolality of 290-300 mOsmoles). This may be attained by addition of sodium chloride or other co-solvents as listed above, or excipients such as buffering agents and antioxidants, as listed above. Injectable formulations are sterilized and, in one embodiment, supplied in single-use vials or ampules. In another embodiment, injectable products may be supplied as sterile, freeze-dried solids for reconstitution and subsequent injection.

In another embodiment, the composition may be delivered to or through the lens of an eye in need of treatment via a contact lens (e.g. Lidofilcon B, Bausch & Lomb CW79 or DELTACON (Deltafilcon A) or other object temporarily resident upon the surface of the eye. For example, U.S. Pat. No. 6,410,045 describes a contact lens-type drug delivery device comprising a polymeric hydrogel contact lens containing drug substance in a concentration of between 0.05% and 0.25% by weight absorbed in said contact lens which is capable of being delivered into the ocular fluid.

In other embodiments, supports such as a collagen corneal shield (e.g. BIO-COR dissolvable corneal shields, Summit Technology, Watertown, Mass.) can be employed. The compositions can also be administered by infusion into the eyeball, either through a cannula from an osmotic pump (ALZET®, Alza Corp., Palo Alto, Calif.) or by implantation of timed-release capsules (OCCUSENT®) or biodegradable disks (OCULEX®, OCUSERT®) which contain the compositions. These routes of administration have the advantage of providing a continuous supply of the composition to the eye.

Several other types of delivery systems are available that are particularly suitable for delivering pharmaceutical compositions to the interior or posterior of the eye. For instance, U.S. Pat. No. 6,154,671 to Parel et al. discloses a device for transferring a medicament into the eyeball by iontophoresis. The device utilizes a reservoir for holding the active agent, which contains at least one active surface electrode facing the eye tissue lying at the periphery of the cornea. The reservoir also has a return electrode in contact with the patient's partly closed eyelids. U.S. Pat. No. 5,869,079 to Wong et al. discloses combinations of hydrophilic and hydrophobic entities in a biodegradable sustained release ocular implant. In addition, U.S. Pat. No. 6,375,972 to Guo et al., U.S. Pat. No.

5,902,598 to Chen et al., U.S. Pat. No. 6,331,313 to Wong et al., U.S. Pat. No. 5,707,643 to Ogura et al., U.S. Pat. No. 5,466,233 to Weiner et al. and U.S. Pat. No. 6,251,090 to Avery et al. each describes intraocular implant devices and systems that may be used to deliver pharmaceutical compositions comprising compounds of the present invention.

U.S. Pat. No. 4,014,335 describes an ocular drug delivery device placed in the cul-de-sac between the sclera and lower eyelid for administering the drug and acting as a reservoir. The device comprises a three-layered laminate of polymeric materials holding the drug in a central reservoir region of the laminate. The drug diffuses from the reservoir through at least one of the polymeric layers of the laminate.

Solid devices, in the form of ocular inserts, have been utilized for longer term symptomatic relief of dry eye. These devices are placed in the eye and slowly dissolve or erode to provide a thickened tear film. Examples of this technology are given in U.S. Pat. Nos. 5,518,732; 4,343,787, and 4,287,175.

Many types of drug delivery systems are known in the art and can be used for delivery of compositions of the present invention. Non-limiting examples have been set forth above.

Dosing

One skilled in the art may recommend a dosage schedule and dosage amount adequate for the subject being treated. The dosing may occur less frequently if the compositions are formulated in sustained delivery vehicles, or are delivered via implant. For topical delivery, it may be preferred that dosing occur one to four times daily for as long as needed. The dosage amount may be one or two drops per dose. The dosage schedule may also vary depending on the active drug concentration, which may depend on the needs of the patient. It may be preferred that the active amount be from about 0.1% to about 10.0% weight by volume in the formulation. In some embodiments, it is preferable that the active drug concentration be 0.25% to about 10.0% weight by volume. The concentration of sterculic acid, or the pharmaceutically acceptable salt form thereof, will preferably be in the range of about 0.1 $\mu$M to about 10 mM in the tissues and fluids. In some embodiments, the range is from 1 $\mu$m to 5 mM, in other embodiments the range is about 10 $\mu$M to 2.5 mM. In other embodiments, the range is about 50 $\mu$M to 1 mM. Most preferably the range of sterculic acid, or the pharmaceutically acceptable salt form thereof, will be from 1 to 100 $\mu$M. The concentrations of the components of the composition are adjusted appropriately to the route of administration, by typical pharmacokinetic and dilution calculations, to achieve such local concentrations.

An ophthalmologist or one similarly skilled in the art will have a variety of means to monitor the effectiveness of the dosage scheme and adjust dosages accordingly. Effectiveness in the treatment of macular degeneration or other retinopathies may be determined by improvement of visual acuity and evaluation for abnormalities and grading of stereoscopic color fundus photographs. (Age-Related Eye Disease Study Research Group, NEI, NIH, AREDS Report No. 8, 2001, Arch. Ophthalmol. 119: 1417-1436). Following such evaluation, the ophthalmologist may adjust the frequency and/or concentration of the dose, if needed.

The present invention will be more readily understand by reference to the following examples, which are not intended to be limiting. Those skilled in the art will readily understand that modifications to the following examples can be made without departing from the scope of the invention.

EXAMPLES

Chick Chorioallantonic Membrane (CAM) Assay:
Method:

Fertilized chick embryos, 9-day old, were maintained in a 48 place table top egg incubator at 37° C. in a specific humidity of 60%. After swabbing the egg shell with 70% alcohol, a small window was cut through the egg shell close to the inner shell surface where the prominent blood vessels are located using a hobby grinding wheel (Dremel Emerson Electric Co., Racine, Wis.). A filter disc saturated with bFGF (5 ng/ml) was placed on the CAM. Sterculic acid dissolved in dimethyl sulfoxide (DMSO) at various concentrations was added to the disc daily over 3-day period of incubation. The controls received the same amount of DMSO. After 72 h the disc and surrounding CAM were excised, inverted and examined under a high power dissecting microscope. The result was reported as reduction in angiogenic stimulation (vessels counted) compared to untreated controls.

Results:

The efficacy of sterculic acid in inhibiting angiogenesis was determined using CAM assay. The number of angiogenesis nodules or blood vessels was determined as a measure of angiogenesis. bFGF at 5 ng/ml induced a significant increase in the number of blood vessels surrounding the disc as compared to controls (FIG. 1). Interestingly, sterculic acid, a cyclopropene fatty acid, inhibited the increase in blood vessels induced by bFGF in a concentration-dependent manner. Significant decrease in blood vessels was observed with 1 $\mu$g/ml of sterculic acid, and more than 3-fold decrease was observed with 10 $\mu$g/ml of sterculic acid. DMSO by itself did not inhibit the blood vessel growth induced by bFGF.

Discussion:

The in vivo/in vitro CAM assay was used to test efficacy of both pro- and antiangiogenic agents. Typically, the assays were performed by growing tissue grafts or cell lines on the intact chick chorioallantoic membrane. The foreign tissue stimulates vascularisation of its surroundings, and counting the decreases or increases in blood vessels entering the graft using a stereomicroscope determine the anti-angiogenic potential of the compounds. Our results show that sterculic acid inhibits the neovascularisation of the chick chorioallantonic membrane demonstrating that this compound exhibits a potent anti-angiogenic activity.

Growth Inhibition Assay:
Method and Results:

HUVEC (1.5×10$^3$) are plated in a 96-well plate in 10 $\mu$L of EBM-2 (Clonetic #CC3162). After 24 h (day 0), the test compound (100 $\mu$L) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water, and air-dried. The stain is eluted with 1:1 solution of ethanol:0.1M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). IC$_{50}$ (drug concentration causing 50% inhibition) is calculated from the plotted data. Sterculic acid demonstrated an IC$_{50}$ of 18.60 $\mu$M. Significant difference in the inhibition was observed with the concentration and the time point tested. The IC$_{50}$ value of the anti-proliferative effect for steculic acid at 72 h was about 11.7 $\mu$M, which is similar to the value observed in the CAM assay (10 $\mu$M).

Discussion:

The antiangiogenic effect of drugs is often associated with their anti-proliferative effects, as proliferation is one of the major events in angiogenesis. Our data show that sterculic acid inhibits the growth of HUVEC by slowing down proliferation, while inducing no apoptosis. $IC_{50}$ values obtained with sterculic acid in HUVE cells are little higher or on par with those reported for compounds to be considered to exert their anti-angiogenic activity by inhibition of endothelial cell proliferation. Thus suggesting that the anti-angiogenic potential of sterculic acid is not to be ruled out and it might be useful in inhibiting angiogenesis in vivo.

Cord Formation Assay:

Method:

Matrigel (60 μl of 10 mg/ml; Collaborative Lab #35423) was placed in each well of an ice-cold 96-well plate. The plate was allowed to sit at room temperature for 15 minutes then incubated at 37° C. for 30 minutes to permit the Matrigel to polymerize. In the meantime, HUVEC were prepared in EGM-2 (Clonetics #CC3162) at a concentration of $2\times10^5$ cells/ml. Sterculic acid was prepared at 2× the desired concentration in the same medium. Cells (500 μl) and 2× drug (500 μl) are mixed and 200 μl of this suspension was placed in duplicate on the polymerized Matrigel. After 24 h incubation, triplicate pictures were taken for each concentration using a Bioquant Image Analysis system. Drug effect ($IC_{50}$) was assessed compared to untreated controls by measuring the length of cords formed and number of junctions.

Results:

The final event during angiogenesis is the organization of endothelial cell in a three-dimensional network of tubes. In vitro, endothelial cells plated on Matrigel align themselves forming tube-like structures. Sterculic acid was able to inhibit HUVEC alignment and cord formation. The concentration of sterculic acid yielding a complete inhibition of endothelial morphogenesis on Matrigel was less or equal to the range of $IC_{50}$ value of 100 μM. The concentrations required to inhibit the cord formation of HUVEC, did not affect their viability (data not shown).

Discussion:

One of the most specific tests for angiogenesis is the measurement of the ability of endothelial cells to form three-dimensional structures (tube formation). Our data indicate that sterculic acid inhibits capillary-like cord formation by endothelial cells at concentrations that are higher than that of other previously described inhibitors of angiogenesis. The concentrations required for a complete abrogation of tubulogenesis were higher than that required to inhibit cell proliferation. Therefore, although a role of the inhibition of endothelial cord formation of sterculic acid could not be discarded, our results suggest that sterculic acid anti-angiogenic activity could be depend on its ability of preventing endothelial cell proliferation more than that of capillary-like cord formation. Taking into account that sterculic acid interferes with endothelial cord formation at a concentration that do not cause death, this compound could be considered an anti-angiogenic compound.

Cell Migration (Chemotaxis) Assay:

Method:

Cell migration was assessed using the 48-well Boyden chamber and 8 μm pore size collagen-coated (10 μg/ml rat tail collagen; Collaborative Laboratories) polycarbonate filters (Osmonics, Inc). The bottom chamber wells received 29 μl of DMEM medium alone (baseline) or medium containing chemoattractant (VEGF). The top chambers received 45 μl of HUVEC cell suspension ($1\times10^6$ cells/ml) prepared in DMEM+1% BSA with or without sterculic acid. After 5 h incubation at 37° C., the membrane was rinsed in PBS, fixed and stained Diff-Quick solutions. The filter was placed on a glass slide with the migrated cells facing down and cell on top were removed using Kimwipe. The testing was performed in 4 replicates and five fields were counted from each well. The data was plotted as mean migrated cells±SD. $IC_{50}$ was calculated from the plotted data.

Results:

Endothelial cell migration plays an important role in vascular budding during angiogenesis. To determine whether sterculic acid could inhibit endothelial cell migration, a chemotaxis assay was carried out using VEGF as chemoattractant. Less than 100 μM of sterculic acid significantly inhibited the VEGF-induced endothelial cell migration, without showing significant cell toxicity. Our results show that sterculic acid inhibits the endothelial cell migration at concentration that is similar to the concentration by which other anti-angiogenic compounds such as α-tocotrienol inhibited the endothelial cell migration.

Discussion:

Cell migration may be evaluated using several different methods; the most widely accepted being the Boyden Chamber assay. In this study, it was demonstrated that sterculic acid inhibits endothelial cell migration. The inhibitory effect of sterculic acid was caused by the inhibition of cell attachment to polycarbonate filters precoated with collagen, suggesting that an antiangiogenic effect of sterculic acid was caused by the inhibition of endothelial cell migration. Also, it has been shown that the migration response was critically dependent on preincubation of the cells with anti-angiogenic compounds. Variation in preincubation time could therefore generate large differences between our results to that of known compounds.

NCI In Vitro Anti-Cancer Cell Line Screening:

Method:

The human tumor cell lines used in the cancer screen panel were grown in RPMI 1640 medium containing 5% FBS and 2 mM L-glutamine. The cells were inoculated into 96-well microtiter plates in 100 μl at plating density ranging from 5000 to 40,000 cell/well. After cell inoculation, the plates were incubated at 37° C. in a humid atmosphere of 5% $CO_2$ for 24 h prior to addition of sterculic acid. Following drug addition, the plates were incubated for an additional 48 h. The assay was terminated by the addition of cold 10% TCA. The supernatant was discarded, and the plates were washed five times with water and air dried. Sulforhodamine B (SRB) solution (100 μl) at 0.4% (w/v) in 1% acetic acid was added to each well, and plates were incubated for 10 min at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. Growth inhibition of 50% ($GI_{50}$) was calculated from the drug concentration resulting in a 50% lower net protein in the treated cells as compared to the net protein seen in the control cells.

Results:

Sterculic acid was subjected to the NCI's in vitro anti-cancer cell line screen. In the NCI screen, 60 human tumor cell lines were treated for 48 h with 10-fold dilution of sterculic acid at a minimum of five concentrations (0.01-100 μM). A sulforhodamine B (SRB) end point was used to calculate the median growth inhibition ($GI_{50}$). $GI_{50}$ refers to the concentration at which the drug inhibits tumor cell growth by 50%. In the NCI anti-cancer cell line screen, sterculic acid has showed a broad spectrum of activity, as well as distinctive patterns of selectivity. As shown in Table 1, this compound is highly effective in leukemia, renal and non-small cell lung cancer at 10 µM, and showed 50% inhibition at lower concentration (1 µM) in number of other cancer cell lines.

TABLE 1

Mean growth inhibitory concentration ($GI_{50}$, µM) of Sterculic acid in the NCI in vitro anti-cancer cell line screen.

| Human Cancer Cell Line | $GI_{50}$ |
| --- | --- |
| Leukemia, SR-91 | 10 µM |
| Leukemia, HL-60 (TB) | 10 µM |
| Non-Small Cell Lung Cancer, NCI-H226 | 10 µM |
| Colon Cancer, HCC-2998 | 10 µM |
| Colon Cancer, SW-620 | 1 µM |
| Melanoma, LOX-IMVI | 1 µM |
| Melanoma, UACC-62 | 1 µM |
| Renal Cancer, RXF-393 | 10 µM |
| Breast Cancer, NCI/ADR-RES | 10 µM |

Discussion:

Angiogenesis plays a key role in tumor growth and metastasis, and neovascularization is a critical determinant of metastatic potential of neoplasms. A practical strategy in preventing recurrence and metastasis is inhibition or impairment of angiogenesis in the early stages of tumor development. The effects of sterculic acid on the growth of 60 different human cell lines was examined. Sterculic acid showed moderate selectivity towards number of cancer cell lines and especially effective against colon cancer and melanoma cell lines based on $GI_{50}$ values, suggesting the anti-angiogenic potential of sterculic acid.

Microarray-Based Analysis of Anti-Angiogenic Activity of Sterculic Acid:

Method:

Human retinal pigment epithelial (RPE) cells (ARPE-19) obtained from ATCC (Manassas, Va.) were grown in Dulbecco's Modified Eagle's Medium (DMEM) containing nutrient mixture F12 (Cellgro, Va.) supplemented with 5% fetal bovine serum, penicillin (100 U/ml) and streptomycin (100 µg/ml). Cells were seeded at a density of $2 \times 10^5$ cells/ml in complete medium and allowed to grow overnight. The culture medium was replaced next day with fresh medium before treating with 10 µM of sterculic acid dissolved in DMSO. The controls received the same amount of DMSO. After 72 h, total RNA, 100 ng, was amplified according to Affymetrix's small sample protocol, and 20 µg of cRNA was then hybridized on each NEI GeneChip microarray. After hybridization, GeneChip array was washed, stained with streptavidin-PE (Molecular Probes), amplified with biotinylated anti-streptavidin antibody and scanned with an argon ion Confocal Laser at 570 nm (Affymetrix). Affymetrix GeneChip Operating software was used for absolute expression and to normalize the gene expression levels between any two samples. Data were then incorporated into GeneSpring software 7.2 (Silicon Graphics) for chip normalization, filtering and cluster analysis.

Results:

To explore the anti-angiogenic mechanism of sterculic acid, the gene expression profile of sterculic acid treated human RPE (ARPE-19) cells using cDNA microarray analysis was investigated. The array includes growth factors and their receptors, chemokines and cytokines, matrix and adhesion molecules, proteases and inhibitors, as well as transcription factors, all involved in the development of blood vessels. Numerous genes were up- or down-regulated in response to sterculic acid by at least 2-fold. The data are summarized in Table 2. Among these genes, transforming growth factor-β (TGF-β), activating transcription factor-4 (ATF-4), growth arrest and DNA damage inducible transcription factor 45B (GADD45B) were down regulated by more than 15, 8 and 7-fold, respectively. On the other hand, sterculic acid treatment increased the expression superoxide dismutase (SOD), cathepsin, BMP7, aldehyde dehydrogenase 7 and heat shock 90 KDa protein. It is evident by the observation that sterculic acid inhibits genes that are pro-angiogenic, and activates genes that are anti-angiogenic.

TABLE 2

List of selected genes differentially expressed during microarray analysis in sterculic acid treated human RPE cells.

| Symbol | Gene Name | Gene Function | Fold Change |
| --- | --- | --- | --- |
| Down-Regulated Genes | | | |
| TGF-β | Transforming growth factor- β | cell growth, differentiation | 15 |
| HYOU1 | Hypoxia up-regulated protein 1 | heat Shock response | 10 |
| CRABP1 | Cellular retinal binding protein | differentiation and proliferation | 8 |
| MT1H | Metallothionein | cell growth, apoptosis | 8 |
| GADD45B | Growth arrest and DNA damage | cell growth, apoptosis | 7 |
| MMP2 | Matrix metalloproteinase | angiogenesis and differentiation | 7 |
| ATF4 | Activating transcription factor 4 | cell growth, differentiation | 7 |
| ALDH3A1 | Aldehyde dehydrogenase 3 | detoxification, lipid peroxidation | 7 |
| IGFBP3 | Insulin-like growth factor BP | cell growth, signal transduction | 3 |
| Up-Regulated Genes | | | |
| ALDH7A1 | Aldehyde dehydrogenase | retinoid synthesis, visual cycle | 15 |
| HSPCA | Heat shock 90 KDa protein | cell signaling, cell viability | 11 |
| CTSC | Cathepsin c | immune/inflammation | 9 |
| BMP7 | Bone morphogenic protein 7 | signaling, cell growth | 6 |
| SCEL | Sciellin | vascular disease | 5 |
| PALLD | Palladin | cytoskeleton, focal adhesions | 5 |
| SOD1 | Superoxide dismutase | oxidative stress | 5 |
| GOT2 | Glutamicoxaloacetic transaminase | response to lipid hydroperoxide | 5 |
| VBP1 | von Hippel-Lindau protein | chaperone and protein folding | 5 |
| FNTA | Farnesyl transferease | cell proliferation, signaling | 4 |
| SUOX | Sulfite Oxidase | cell viability | 3 |

Discussion:

DNA Microarray analysis was used to investigate the effect of sterculic acid on the gene expression profile of cultured human RPE cells. The microarray-based gene expression analysis of RPE cells reveled that a large number of genes is involved in anti-angiogenesis induced by sterculic acid. Interestingly, number of angiogenesis-related genes, including TGF-β and MMP-2, were strongly down regulated and some known angiogenesis-inhibitory genes were significantly increased, suggesting that these genes may be critical mediators of sterculic acid-induced anti-angiogenesis. These result further show that sterculic acid possesses anti-angiogenic effect through regulating genes involved in the angiogenic process.

Evaluation of the Anti-Angiogenic Properties of Antagonists to 7-Ketocholesterol-Mediated Inflammation in the Laser-Induced Choroidal Neovascularization (CNV) Rat Model Laser-induced CNV, flat mount preparations, and lesion evaluations were performed following established methods. Amaral et al. A novel imaging technique for experimental choroidal neovascularization. IOVS 2006; 47:5163-5170. Experimental CNV was induced by laser breakage of Bruch's membrane in Brown Norway rats. Neovessels were visualized with confocal microscopy using choroid/RPE flat mounts labelled with Alexa Fluor 568-Isolectin IB4 to identify endothelial cells and neovessel volumes were quantified using VOLOCITY software. In one paradigm, forty eight hours after laser exposure, a single intravitreal injection (IV) was administered (1 mM in 1 µL IV injection). Animals were sacrificed at day 7.

For the second paradigm, immediately after laser exposure, drops containing sterculic acid were immediately applied, followed by daily dosing for 6 days. Doses tested were 0.1 mM, 1 mM, and 10 mM drops. Animals were sacrificed at day 7.

Forty eight hours after laser exposure, a single intravitreal injection (IV) was administered (1 mM in 1 µL IV injection). Animals were sacrificed at day 7.

Figure 2:
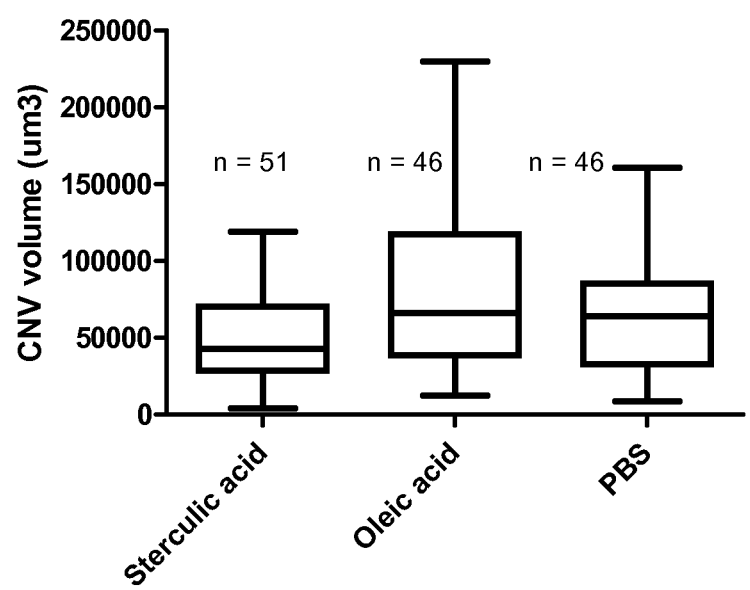
FIG. 2 depicts the results of choroidal neovascularization (CNV) suppression after a single intravitreal injection 48 hours after laser exposure. Box-and-whisker plot representations of volume of CNV lesions from rats treated with a single intravitreal injection as indicated in the x-axis. The y-axis represents neovessel lesion volume expressed in cubic microns. The number of lesions evaluated per condition (n) is depicted in the graph. Values inside of the box represent the central 50% of measurements. The horizontal line inside the box corresponds to the median values, and the vertical lines outside the boxes correspond to variances of measurements. *Highly significant difference compared with oleic acid and PBS.

FIG. 2 demonstrates CNV suppression after a single intravitreal injection 48 hours after laser exposure. The results indicate that 1 mM sterculic acid suppresses 33% CNV compared to oleic acid and PBS injection ($p \leq 0.016$).

Figure 3A:
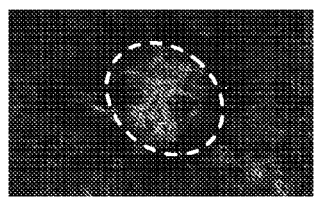
FIG. 3 depicts the results of daily application of sterculic acid-containing drops to suppress laser-induced CNV. (A) Representative flat-mount projections from confocal microscope Z-series 7 days after laser. The red channel identifies vessels (Isolectin IB-4). Conditions are indicated above each projection. (B) Box-and-whisker plot representations of volume of CNV lesions from rats treated with daily drops as indicated in the x-axis. The y-axis represents neovessel lesion volume expressed in cubic microns. The number of lesions evaluated per condition (n) is depicted in the graph. Values inside of the box represent the central 50% of measurements. The horizontal line inside the box corresponds to the median values, and the vertical lines outside the boxes correspond to variances of measurements. *Significant or **highly significant difference compared with PBS, laser control or oleic acid.
Figure 3A:
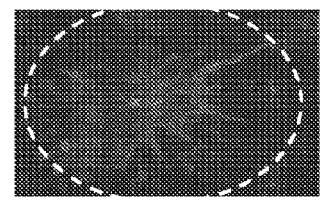
Figure 3B:
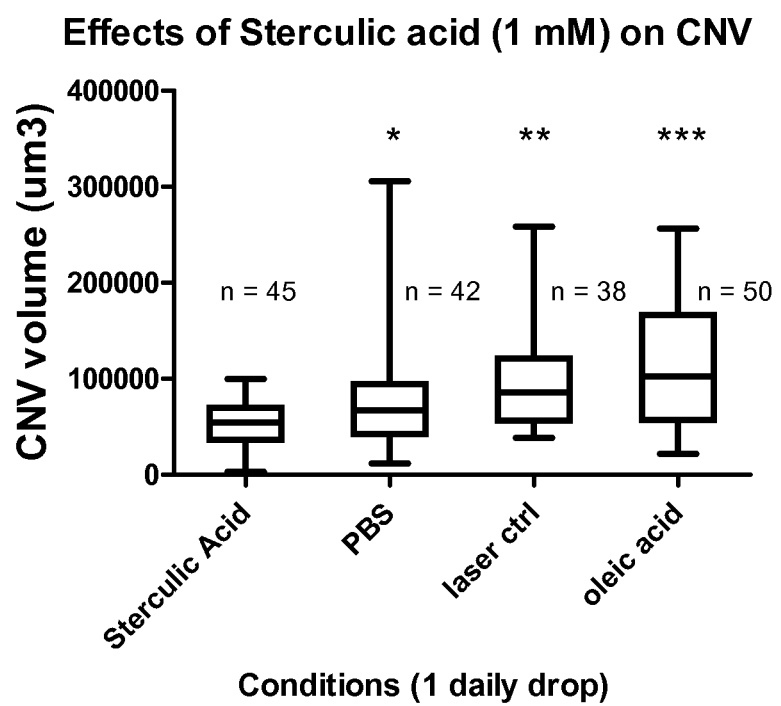

FIG. 3 demonstrates CNV suppression after daily treatment with sterculic acid-containing drops after laser exposure. These results indicate that 1 mM sterculic acid suporesses 45% CNV as compared to oleic acid ($p \leq 0.00000002$).

Figure 4A:
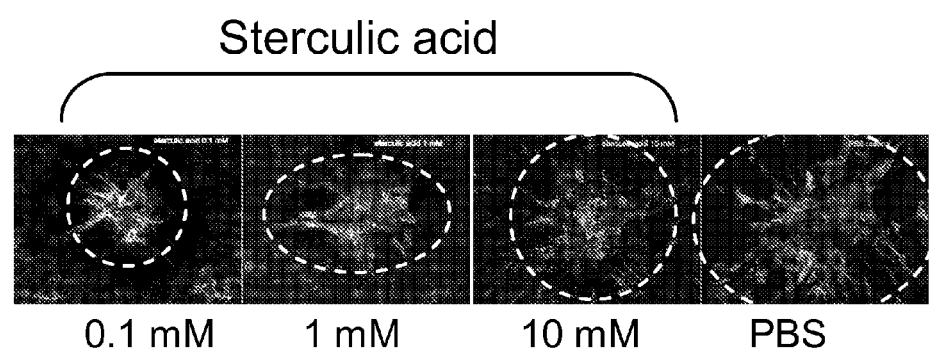
FIG. 4 depicts the dose response of CNV suppression after daily application of sterculic acid-containing drops after laser exposure. (A) Representative flat-mount projections from confocal microscope Z-series 7 days after laser. The red channel identifies vessels (Isolectin IB-4). Conditions are indicated below each projection. (B) Box-and-whisker plot representations of volume of CNV lesions from rats treated with daily drops as indicated in the x-axis. The y-axis represents neovessel lesion volume expressed in cubic microns. The number of lesions evaluated per condition (n) is depicted in the graph. Values inside of the box represent the central 50% of measurements. The horizontal line inside the box corresponds to the median values, and the vertical lines outside the boxes correspond to variances of measurements. *Significant or **highly significant difference compared with PBS.
Figure 4B:
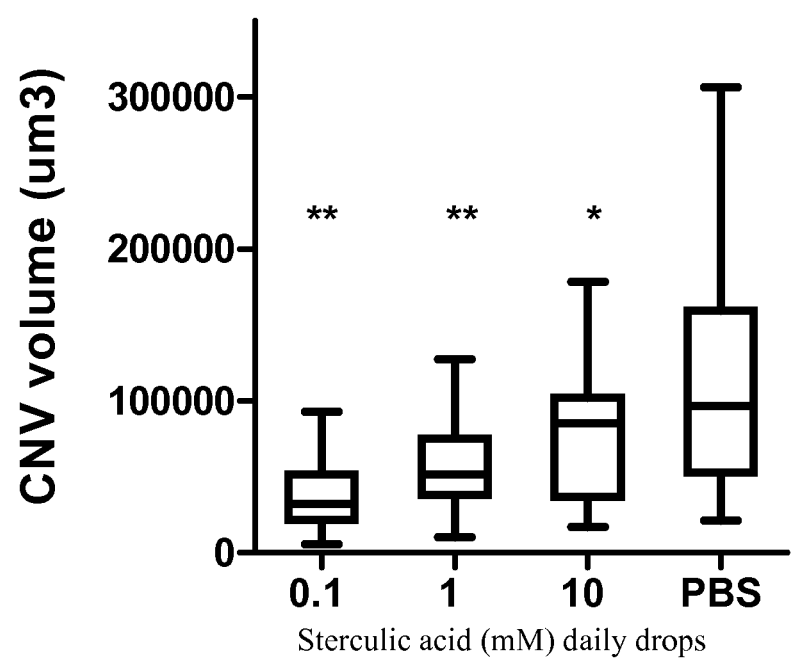

FIG. 4 demonstrates the dose response of CNV suppression after daily sterculic acid drops. The results indicate that 0.1 mM sterculic acid suppresses 66% CNV as compared to PBS ($p \leq 0.0001$).

These results indicate that a single intravitreal injection of sterculic acid was effective in partially suppressing CNV. Importantly, sterculic acid drops were able to traverse the sclera, reaching the choroids at therapeutic levels and inducing a 66% suppression of CNV.

Evaluation of the Protective Effect of 1 µM Sterculic Acid on 7-Ketocholesterol-Induced Cytotoxicity Using ARPE19 Cells.

Materials:

Human retinal pigmented epithelium (ARPE19) cells were purchased from ATCC (Manassas, Va.). DMEM/F12 medium (50:50) was purchased from Mediatech Inc, Manassas, Va. Fetal bovine serum and penicillin/streptomycin were purchased from Invitrogen Corp. (Carlsbad, Calif.). Sterculic acid was purchased from Biofine International Inc. (Blain, Wash.). 7-Ketocholesterol (7KCh) was purchased from Steraloids, Inc. (Newport, R.I.). Dihydrosterculic acid was purchased from Matreya LLC (Pleasant Gap, Pa.). Hydroxypropyl-β-cyclodextrin (HPBCD), dichlormethane and DMSO were purchased from Sigma-Aldrich (St. Louis, Mo.). Oleic acid and ethanol were purchased from Acros Oganics (Geel, Belgium). For cell viability assay, Cell Counting Kit-8 (CCK-8) was purchased from Dojindo Molecualr Technologies, Inc. Rockville, Md. and CellTiter-Glo® Luminescent Cell Viability Assay was purchased from Promega, Madison, Wis.

Methods:

Preparation of 7-Ketocholesterol Solution in HPBCD (see Moreira E F, Larrayoz I M, Lee J W, Rodriguez I R. 7-Ketocholesterol is present in lipid deposits in the primate retina: Potential implication in the induction of VEGF and CNV formation. *Invest Ophthamol Vis Sci.* 2009; 50(2):523-532.). HPBCD-7KCh solutions were prepared as follows. 7KCh was weighed and wetted with dichloromethane and then was dissolved in the smallest volume possible of 100% ethanol. HPBCD (45% wt/vol) was dissolved in PBS and added to the 7KCh-ethanol solution in a glass graduated cylinder. The 45% HPBCD was added to the final volume required for 10 mM 7KCh solution. The solution was vigorously mixed and put into a 42° C. oven to allow the ethanol and any lingering dichloromethane to evaporate. The HPBCD-7KCh solution was then adjusted to a final volume using distilled water. The 10 mM 7KCh solution was diluted to 1 mM using PBS, and this solution was added to the cells directly.

Preparation of Fatty Acid Solution:

Sterculic acid (SA, MW:294.5), dihydrosterculic acid (DHSA, MW:296) and oleic acid (OA, MW:282) were dissolved in 100% DMSO to make 10 mM. Further, each fatty acid solution was diluted in 1:10 in DMSO to make 1 mM.

Cell Cultures:

ARPE-19 cells were cultured in DMEM/F12 medium (50:50) containing 10% fetal bovine serum (FBS), 2 mM glutamine, 100 IU/ml penicillin, and 100 µg/ml streptomycin. The cells were incubated at 37° C. in a humidified 5% $CO_2$ atmosphere.

Drug Treatment and Cytotoxicity Assessment:

Cell-based assays have been used as suitable substitute methods for animal experiments in pre-clinical research and development of drugs and toxicological testing. In order to measure cell viability, different methods were performed as follows.

1. Microelectronic Cell Sensor Assay (RT-CES® System, ACEA Biosciences Inc, San Diego, Calif.)

(Xing, J. Z., Zhu, L., Jackson, J. A., Gabos, S., Sun, X. J., Wang, X. B., Xu, X., 2005. Dynamic monitoring of cytotoxicity on microelectronic sensors. Chemical Research in Toxicology 18, 154-161.)

RT-CES® System is a cell-based assay system that monitors cellular events by measuring the electronic impedance of sensor electrodes integrated on the bottom of microtiter E-Plates. The presence of the cells will lead to an increase in the electrode impedance. The more cells attached to the sensor, the higher the impedance that could be monitored with RT-CES.

1) Cells were cultivated in the ACEA's 16X E-plate device containing microelectrodes at the bottom of each well to measure contact area and electrical properties of adherent cells.

2) Background signals were blanked by measuring culture media impedance (100 µl per well) before seeding cells.

3) The cells (40,000 cells/100 µL) were added to the well and stood for 15 min at room temperature and cultured at 37° C. in a humidified 5% $CO_2$ atmosphere.

4) Cell growth was monitored periodically (every 1 hr) for indicated durations via calculation of a "cell index" (reflect to the surface area covered by the cells) in each well.

5) Approximately 19 hr after seeding, when the cells were in the log growth phase, the cells were treated with either DMSO or 1 µM fatty acid in 200 µL of serum free media and subsequently added with 15 µM 7KCh in HPBCD. The cells were also treated with DMSO and HPBCD, which served as vehicle control. The final DMSO and HPBCD concentrations in the media were in the range of 0.1% and 0.0675%, respectively.

6) The sensor devices were put into the incubator again and the cells were continuously monitored cellular status changes.

7) Cell viability was determined as a cell index (CI) calculated from the impedance of each well automatically by the RT-CES system once per hr until the end of the experiment. The data was normalized at the point immediately prior to compound treatment.

2. Cell Viability Assay

A series cell suspension with the same cell number used for RT-CES system were used to measure cell viability using Cell Counting Kit-8 (Dojindo) and CellTiter-Glo® Luminescent Cell Viability Assay (Promega) according to the manufacturer's protocol.

2-1. Cell Counting Kit-8 (Dojindo Molecualr Technologies, Inc.)

The kit allows sensitive colorimetric assays for the determination of the number of viable cells in cell proliferation and cytotoxicity assays. The amount of the formazan dye generated by the activity of dehydrogenases in cells is directly proportional to the number of living cells.

1) Cells were cultivated in a 96 well cell plate (Costar#3599, Corning Incorp, Corning, N.Y.).

2) The cell suspension (40,000 cells/100 µL) were added to 100 µL culture media per well and stood for 15 min at room temperature and cultured at 37° C. in a humidified 5% $CO_2$ atmosphere.

3) Approximately 19 hr after seeding, when the cells were fully confluent, the cells were treated with either DMSO or 1 µM fatty acid in 200 µL of serum free media and subsequently added with 15 µM 7KCh in HPBCD. Then, the plate was swirled for mixing. The cells were also treated with DMSO and HPBCD, which served as vehicle control. The final DMSO and HPBCD concentrations in the media were in the range of 0.1% and 0.0675%, respectively.

4) After 24 hr treatment, the media was immediately aspirated and the cells were incubated for 2 hr with 100 µL of serum media containing 10 µL of CCK-8 agents per well at 37° C. in a humidified 5% $CO_2$ atmosphere to measure cellular dehydrogenase activity.

5) The absorbance was read at 450 nm in Envision model 2104 multi-labeled reader (Perkin-Elmer, Waltman, Mass.). Cell viability was expressed as the percentage of compound treated cells relative to that of untreated controls. Prior to measure cell viability, the cells were imaged live by Nikon TE 2000-U inverted fluorescent microscope.

2-2, CellTiter-Glo® Luminescent Cell Viability Assay (Promega, Madison, Wis.)

CellTiter-Glo® Luminescent Cell Viability Assay is a homogeneous method of determining the number of viable cells in culture based on quantitation of the ATP (luminescent signal) present, an indicator of metabolically active cells.

1) Cells were cultivated in a 96 well cell plate (Costar#3599, Corning Incorp, Corning, N.Y.).

2) The cell suspension (40,000 cells/100 µL) were added to 100 µL culture media per well and stood for 15 min at room temperature and cultured at 37° C. in a humidified 5% $CO_2$ atmosphere.

3) Approximately 19 hr after seeding, when the cells were fully confluent, the cells were treated with either DMSO or 1 µM fatty acid in 200 µL of serum free media and subsequently added with 15 µM 7KCh in HPBCD. The cells were also treated with DMSO and HPBCD, which served as vehicle control. The final DMSO and HPBCD concentrations in the media were in the range of 0.1% and 0.0675%, respectively.

4) After 24 hr after treatment, the media was immediately aspirated and the cells were added 100 µL of CellTiter-Glo® Reagent to 100 µL of serum free medium in each well. The contents in a plate were mixed for 2 min on an orbital shaker to induce cell lysis.

5) The plate was allowed to incubate at room temperature for 10 min to stabilize luminescent signal.

6) The luminescence was recorded in Envision model 2104 multi-labeled reader (Perkin-Elmer, Waltman, Mass.) with an integration time of 0.1 s/well. Cell viability was expressed as the percentage of compound treated cells relative to that of untreated controls.

Figure 5:
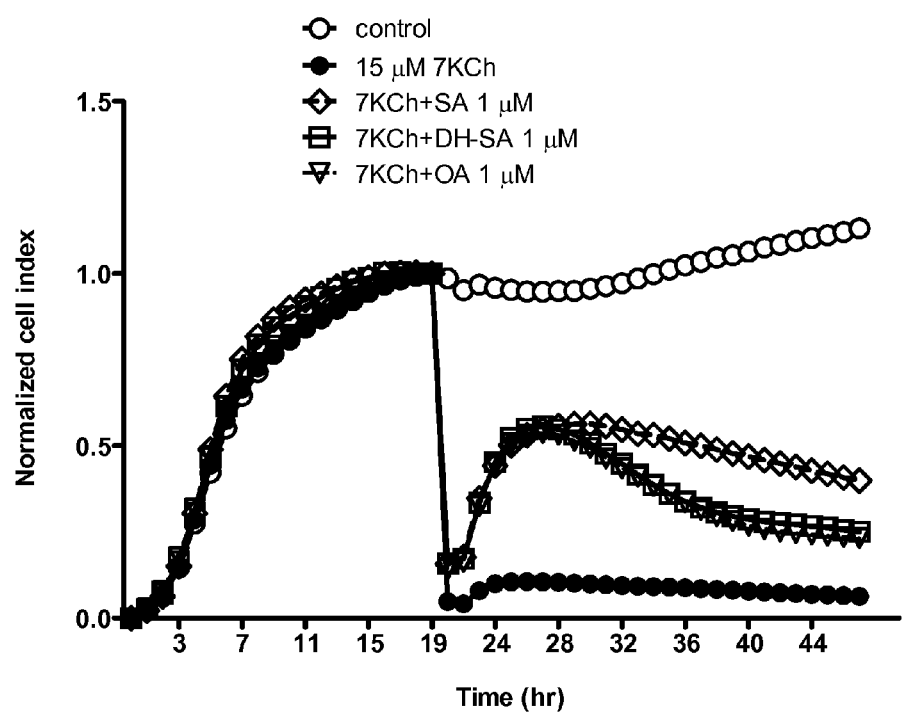
FIG. 5 depicts dynamic monitoring of cytotoxic response to sterculic acid on 7KCh-treated ARPE19cells. $4 \times 10^4$ cells were seeded onto wells of 16× microtiter plates. Cell growth was monitored by RT-CES™ system, and showed steady increases in cell index (an indication of cell growth). At 19 hr after seeding, 1 μM sterculic acid and 15 μM 7KCh in serum free media were added to the cells. Cell viability was determined as a cell index (CI) calculated from the impedance of each well automatically by the RT-CES system once per hr until the end of the experiment. The data was normalized at the point immediately prior to compound treatment.

Results:

Real-time monitoring of cell viability (FIG. 5) showed that 7KCh (15 µM) addition to ARPE19 cells markedly decreased in ARPE19 cells cell index over time, indicating that 7KCh are eliciting a cytotoxic effect upon ARPE19 cells. However, the co-treatment of sterculic acid (1 µM) showed higher cell index than 7KCh alone consistently at all the indicated time points. The results indicated that sterculic acid markedly protected ARPE 19 cells from 7KCh induced cytotoxicity. Dihydrosterculic acid and oleic acid also showed the slight protective effect against cytotoxicity by 7KCh.

Figure 6:
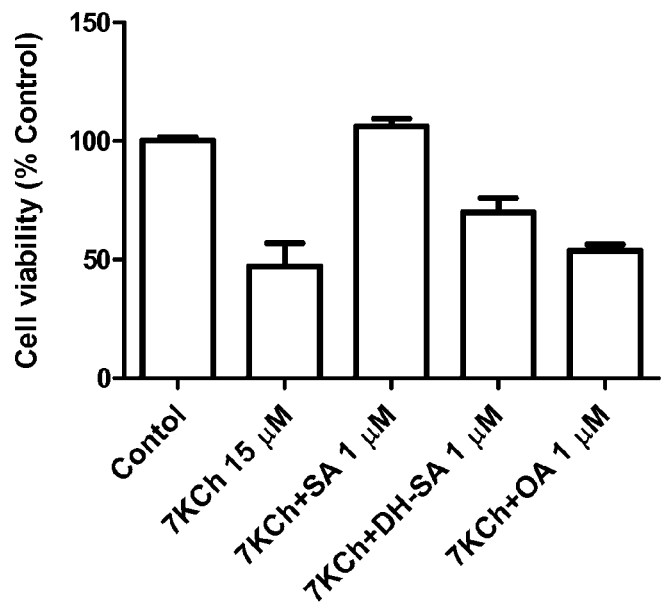
FIG. 6 depicts the protective effect of sterculic acid on 7KCh induced cytotoxicty in ARPE-19 cells (CCK-8). $4 \times 10^4$ cells were seeded onto wells of a 96 well plate. At 19 hr after seeding, the cells were added with 1 μM sterculic acid and 15 μM 7KCh in serum free media and incubated for 24 hr. Cell viability was determined as celluar dehydrogenase activity and expressed as the percentage of compound treated cells relative to that of untreated controls. error bar: standard deviation, n=4.

Cellular (mostly mitochondrial) dehydrogenase activity showed that 15 µM 7KCh caused 50-60% loss in cell viability (FIG. 6). However, co-treatment with sterculic acid (1 µM) marked increased cell viability and maintained similar to the level of untreated control. Dihydrosterculic acid or oleic acid treatment increased 20% and 10% of cell viability compared to 7KCh alone treatment.

Figure 7:
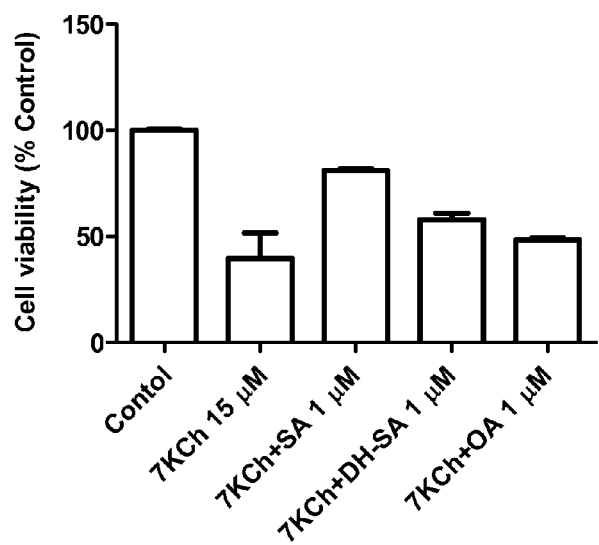
FIG. 7 depicts the protective effect of sterculic acid on 7KCh induced cytotoxicty in ARPE-19 cells (CellTiter-Glo Luminescent). $4 \times 10^4$ cells were seeded onto wells of a 96 well plate. At 19 hr after seeding, the cells were added with 1 μM sterculic acid and 15 μM 7KCh in serum free media and incubated for 24 hr. Cell viability was determined as the ATP (luminescent signal) level and expressed as the percentage of compound treated cells relative to that of untreated controls. Error bar: standard deviation, n=4.

ATP level using CellTiter-Glo® Luminescent assay showed that 15 µM 7KCh caused 40-50% loss in cell viability (FIG. 7). However, co-treatment with sterculic acid (1 µM) increased cell viability and reached 80% to the level of untreated control. Dihydrosterculic acid or oleic acid treatment increased 20% and 10% of cell viability compared to 7KCh alone treatment.

Figure 8:
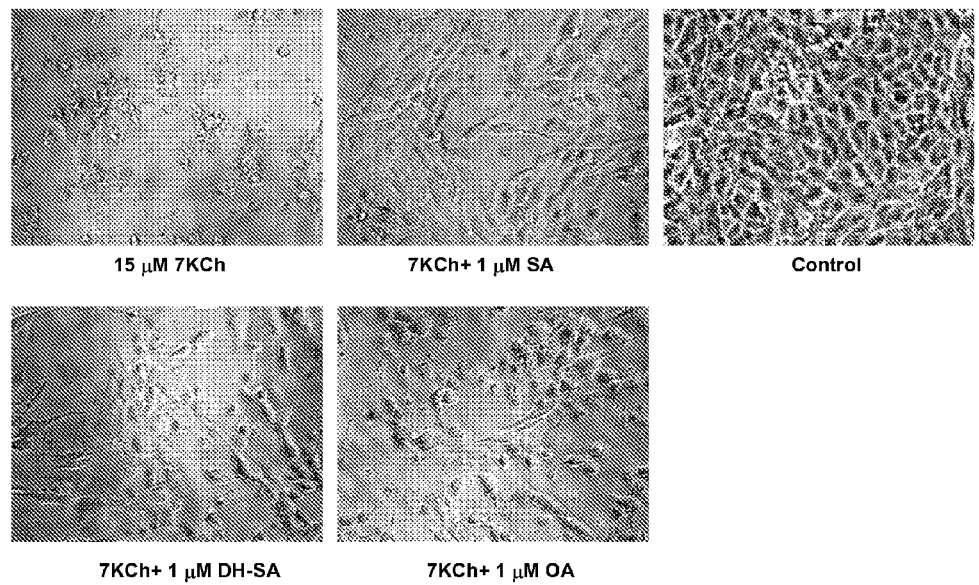
FIG. 8 depicts phase-contrast images of ARPE19 cells at 24 hr after sterculic acid co-treatment with 7KCh. Prior to measure cell viability, the cells were imaged live by Nikon TE 2000-U inverted fluorescent microscope.

Cell morphological changes were observed after 7KCh treatment (FIG. 8). Given 7KCh to the cells, almost a half of cells in the field changed to round and float cell or cell debris. However, compared to 7KCh alone, sterculic acid induced much less proportion of dead cell and cell debris. Dihydrosterculic acid and oleic acid treatment had more cells compared to 7KCh alone.

Treatment of 1 µM sterculic acid which was the most potent among fatty acids tested showed the greatest protective effect against cytotoxicity by 7KCh. Dihydrosterculic acid and oleic acid also showed the slight protective effect against cytotoxicity by 7KCh.

Evaluation of Effects of Sterculic Acid on 7-Ketocholesterol-Mediated Cytotoxicity in Human retinal pigmented epithelium derived cell line ARPE19 and D407

Materials:

7-Ketocholesterol (7KCh) was purchased from Steraloids, Inc. (Newport, R.I.). Pure sterculic acid (MW 294.5) was synthesized by Biofine International Inc (Vancouver, Canada). Dihydrosterculic acid was obtained from Matreya LLC (Pleasant Gap, Pa.). Oleic acid was obtained from Acros Oganics (Geel, Belgium).

Cell Culture:

ARPE19 cells were cultured in DMEM/F12 (Mediatech, Manassas, Va.) containing 10% fetal calf serum (Invitrogen Corp, Carlsbad, Calif.), 2 mM glutamine (Invitrogen), 100 IU/mL penicillin (Invitrogen), and 100 µg/mL streptomycin (Invitrogen) in Costar® 24-well plates (Corning Incorporated, Corning, N.Y.).

D407 cells were cultured in DMEM (Mediatech, Manassas, Va.) containing 4% fetal calf serum (Invitrogen Corp, Carlsbad, Calif.), 2 mM glutamine (Invitrogen), 100 IU/mL penicillin (Invitrogen), and 100 µg/mL streptomycin (Invitrogen) in Costar® 24-well plates (Corning Incorporated, Corning, N.Y.).

Preparation of 7KCh Solutions in HPBCD:

7KCh was weighed and wetted with dichloromethane (Fisher Scientific, Pittsburgh, Pa.) then dissolved in the smallest volume possible of 100% ethanol (Fisher Scientific). HPBCD (45% w/v) was dissolved in PBS and added to the 7KCh-ethanol solution in a glass graduated cylinder. The solution was vigorously mixed and incubated in a 42° C. oven to evaporate the ethanol and any lingering dichloromethane. Distilled water was added to the HPBCD-7KCh solution to make 10 mM 7KCh solution. The 10 mM 7KCh solution was diluted to 1 mM using PBS and this solution was added to the cell cultures directly. The final concentration of HPBCD in cell cultures receiving 10 µM 7KCh is 0.045%. ARPE19 cells tolerate HPBCD concentrations greater than 1% without any toxicity.

Preparation of Sterculic Acid, Dihydrosterculic Acid, and Oleic Acid:

Stock solution was prepared as 10 mM in 100% dimethyl sulphoxide (DMSO, Sigma-Aldrich, St. Louis, Mo.). Further dilution of the stock solution was done with sterilized phosphate buffer saline (PBS, KD Medical, Columbia, Md.). The final working concentrations were $5 \times 10^{-6}$-$5 \times 10^{-7}$ M.

Treatment of 7-Ketocholesterol, Sterculic Acid, Dihydrosterculic Acid, and Oleic Acid and Cell Viability Assay:

Cells were seeded in 24-well plates at a density of $1 \times 10^5$/mL per well and let to rest for 16-24 h. Cells were then exposed to 7-ketocholesterol in serum-free medium with or without sterculic acid, dihydrosterculic acid, and oleic acid for 24 h. In preliminarily experiments, it was determined that the 50% lethal concentration ($LC_{50}$) of 7-ketocholesterol for ARPE 19 and D407 cells are 12 µM and 11 µM respectively. Thus such 7-ketocholesterol concentrations were used in evaluations of the protection effects of sterculic acid, dihydrosterculic acid, and oleic acid.

After 7-ketocholesterol treatments, the cell viability was determined using the Cell Counting Kit-8 (Dojindo Molecular Technologies, Inc., Rockville, Md.) which measures cellular dehydrogenase (mostly mitochondrial) activity. Cell Counting Kit-8 (CCK-8) uses a highly water-soluble tetrazolium salt. WST-8 [2-(2-methoxy-4-nitrophenyl)-3-(4-nitrophenyl)-5-(2,4-disulfophenyl)-2H-tetrazolium, monosodium salt] which produces a water-soluble formazan dye upon reduction in the presence of an electron carrier. The absorbance at 450 nm is proportional to the number of viable cells in the medium and it correlates well with the [3H]-thymidine incorporation assay. The 24-well plates were read using a Envision model 2104 multi-labeled reader (Perkin-Elmer, Waltman, Mass.). The cell viability assays were performed in 24-well plates with each measurement performed in quadruplicate.

Figure 9:
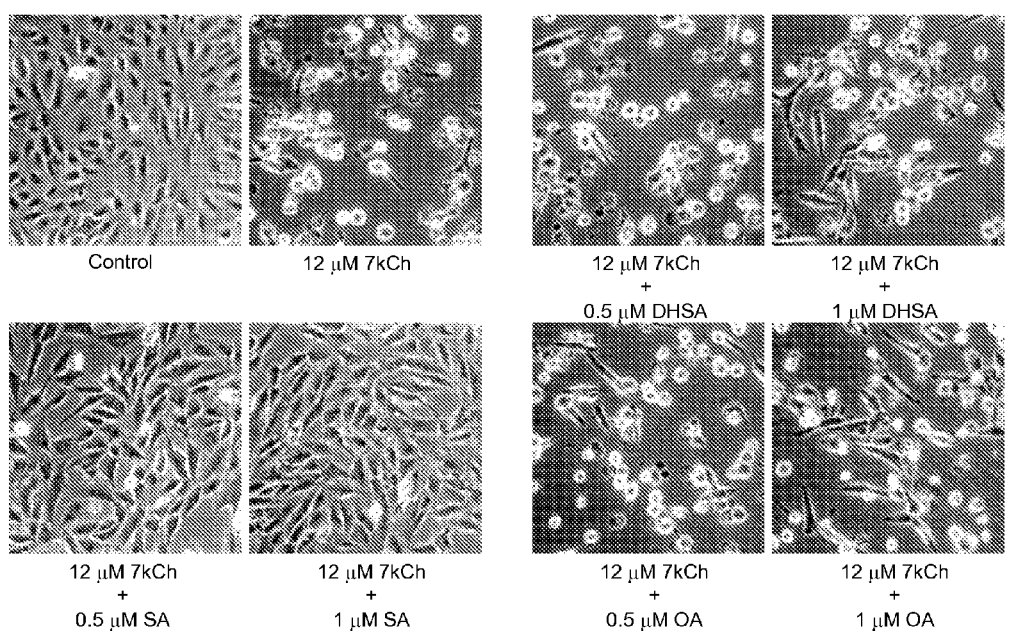
FIG. 9 depicts images of ARPE19 cells incubated in 12 μM ($LC_{50}$) 7-ketocholesterol, with or without sterculic acid, dihydrosterculic acid, and oleic acid for 24 h. Only sterculic acid shows apparent protection of the cells at both 0.5 and 1 μM concentrations. Dihydrosterculic acid and oleic acid do not have such protection effect even at 1 μM concentration.

Images of ARPE19 cells taken after 24 hr treatment with 7KCh show a marked decrease in cell confluency and shrinkage of cells. Co-treatment with sterculic acid of 0.5 and 1 µM apparently maintain both cell confluency and cell morphology similar to the control. Comparing to sterculic acid, the co-treatments with other structural analogues, either dihydrosterculic acid or oleic acid, show no effect at 0.5 µM and a slight effect at 1 µM of concentration (FIG. 9). This suggest sterculic acid is better in protecting cells from 7KCh-induced cytotoxicity than other structural analogues.

Figure 10A:
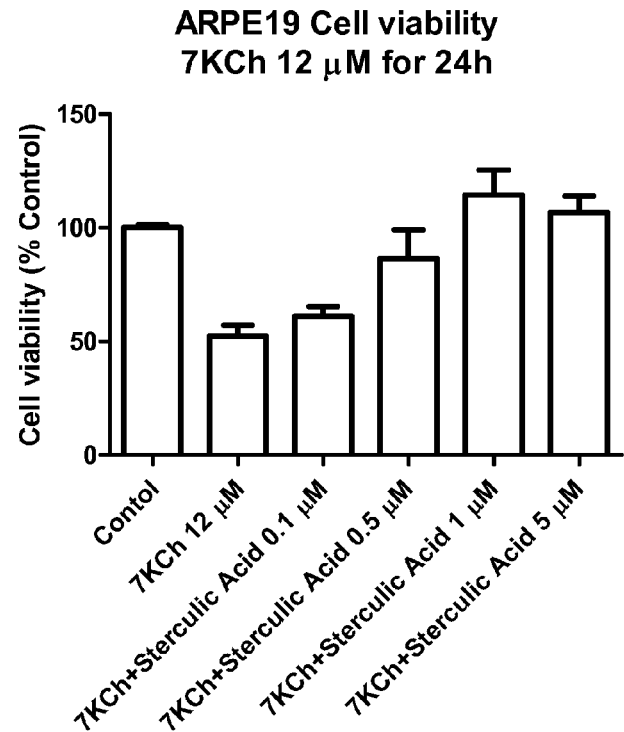
FIGS. 10A and 10B depict a representative protection effect against 12 μM 7-ketocholesterol treatment in ARPE19 cells as a function of sterculic acid and oleic acid concentrations. Apparent protection by sterculic acid is seen at concentrations of 0.5 μM. In addition, the cell viability of ARPE19 with sterculic acid concentration≥1 mM is approximately at the same level as control. The oleic acid shows a slight protection at concentration of 5 μM. Error bar: standard deviation, n=4.
Figure 10B:
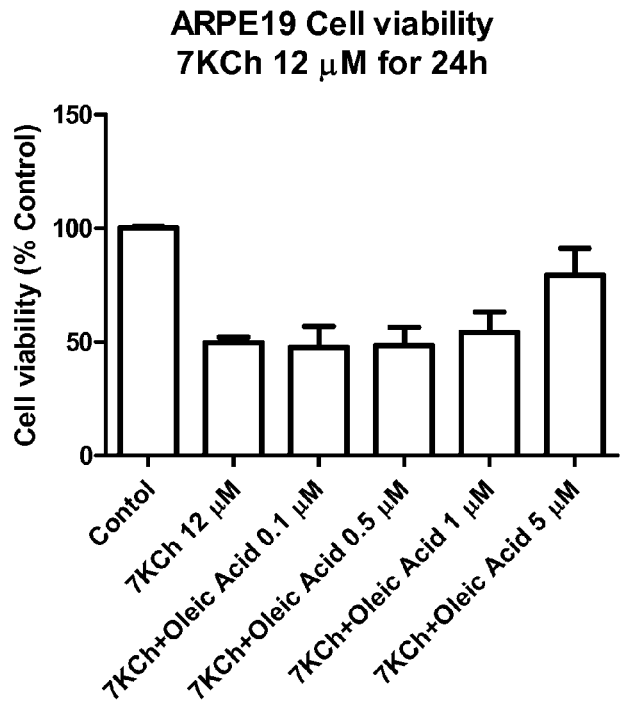
Figure 11A:
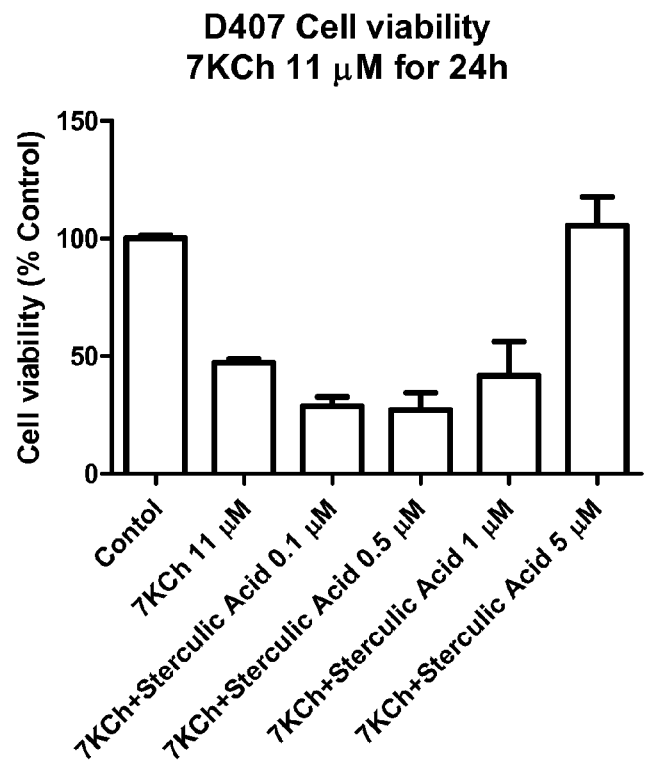
FIGS. 11A and 11B depict representative protection effect against 11 μM 7-ketocholesterol ($LC_{50}$) treatment in D407 cells as a function of sterculic acid and oleic acid concentrations. Apparent protection by sterculic acid is seen at concentrations of 5 μM where the cell viability is approximately at the same level as control. Although oleic acid also shows protection at concentration of 5 μM, the effect is not as significant comparing to sterculic acid. Error bar: standard deviation, n=4.
Figure 11B:
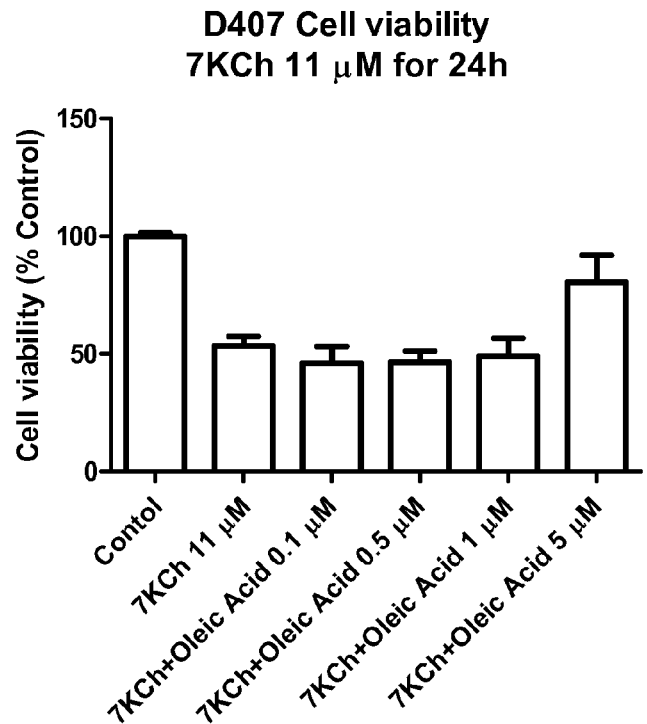

The cell viability assay results further prove the advantage of the usage of sterculic acid. The 24-hr 7KCh treatment decreases the cell viability approximately 50%. But this cytotoxic effect is offset completely by a co-treatment with 1 µM sterculic acid in ARPE19 cells or 5 µM sterculic acid in D407 cells (FIGS. 10A and 11A). Such protection effect is not seen in the co-treatment with oleic acid, which shows only a slight effect at concentration of 5 µM (FIGS. 10B and 11B).

Materials

7KCh was purchased from Steraloids (Newport, R1). Sterculic acid (8-2(2-octacyclopropen-1-yl) octanoic acid, 19Δ:1) was purchased from Biofine International (Vancouver, Canada). Dihydrosterculic acid (DHSA, 19Δ:0) was purchased from Matreya (Pleasant Gap, Pa.). α-linolenic acid (18:3), linoleic acid (18:2), oleic acid (18:1), and stearic acid (18:0) were purchased from Acros Organics (Morris Plains, N.J.). Arachidonic acid (20:4) and docosahexaenoic acid (22:6, DHA) were purchased from Sigma-Aldrich (St. Louis, Mo.). Deuterated cholesterol (D7-Ch) and deuterated 7-ketocholesterol (D7-7K) (25, 26, 26, 26, 27, 27, 27, D7) were purchased from Cambridge Isotope Laboratories, Inc. (Andover, Mass.). The rabbit antibodies for CHOP, GRP78, and the anti-rabbit IgG HRP-linked secondary antibody were purchased from Cell Signaling Technology (Danvers, Mass.). The rabbit antibody for GAPDH was purchased from Abcam (Cambridge, Mass.).

Animals

Eight weeks old male Brown Norway rats weighing around 150 grams were purchased from Charles River Laboratories (Rockville, Md.). All animals were treated according to the ARVO Statement for the Use of Animals in Ophthalmic and Vision Research.

Cell Cultures

ARPE-19 cells (American-Type Culture Collection, Manassas, Va.) were grown in DMEM/F-12 medium (Mediatech, Manassas, Va.) containing 10% FBS, 100 IU/ml penicillin, and 100 µg/ml streptomycin (Invitrogen, Carlsbad, Calif.).

Preparation of 7-Ketocholesterol and Fatty Acids

7KCh was wetted with dichloromethane (Thermo Fisher Scientific, Pittsburgh, Pa.) then dissolved in ethanol (Thermo Fisher Scientific). The 7KCh-ethanol solution was mixed with 45% (w/v) hydroxypropil-β-cyclodextrin (HPBCD, Sigma-Aldrich) dissolved in phosphate buffer saline (PBS, KD Medical, Columbia, Md.). The ethanol and dichloromethane were removed by incubating the solution at 45° C. overnight. The solution volume was then adjusted with distilled water to make a stock solution containing 10 mM 7KCh in 45% HPBCD, 1×PBS. The 10 mM 7KCh solution was diluted to 1 mM with sterilized PBS and this solution was added to the cell cultures directly. The final concentration of HPBCD in cell cultures receiving 10 µM 7KCh was 0.045%. ARPE19 cells tolerate HPBCD concentrations greater than 1% without any toxicity.

Stock solutions of fatty acids were prepared as 10 mM in either dimethyl sulphoxide (DMSO, Sigma-Aldrich) or ethanol. Further dilution of the fatty acid solutions was done with sterilized PBS to make the 100 μM stock solutions and this solution was added to the cell cultures directly. The final working concentrations of fatty acids were 0.1-10 μM.

Treatments of 7-Ketocholesterol and Fatty Acids

ARPE-19 cells were seeded in 24-well plates with $1 \times 10^5$ cells per well and allowed to recover for 16-24 hr. Once confluency reached approximately 90%, the effect of the fatty acids against 7KCh-mediated cell death was examined 24 hr after incubation in serum-free medium with 12 μM 7KCh. Fatty acids were tested at 0.1, 0.5, 1, 5 and 10 μM concentrations. The effects of the fatty acids against 7KCh-mediated inflammation and ER stress were examined by incubating cells in 1 μM fatty acids with either 8 μM 7KCh (24 hr for quantitative real-time PCR (qRT-PCR), 24 and 48 hr for immunoblot), or 6 μM 7KCh for 48 hr (for ELISA). Three individual experiments were performed for each treatment with quadruplicate measurements performed for each experiment in 24-well plates.

Treatments with TNF-α

Tumor necrosis factor-alpha (TNF-α, Roche Diagnostics, Indianapolis, Ind.) was diluted in PBS to make 10 μg/ml stock solution and stored at −20° C. In order to test the anti-inflammation effect of fatty acids against TNF-α, ARPE-19 cells were treated with 2 ng/ml of TNF-α for 24 hr in serum-free medium with or without 1 μM fatty acids. The mRNA expressions of cytokines were then examined using qRT-PCR. Each treatment was performed three times with quadruplicate measurements in each experiment, in 24-well plates.

Cell Viability Assay

The cell viability was determined by the dehydrogenase activity of the ARPE-19 cells using Cell Counting Kit-8 (CCK8, Dojindo, Gaithersburg, Md.) according to manufacturer's protocol.

Quantitative Real-time PCR

The RNA was extracted using RNeasy Mini Kit (Qiagen, Valencia, Calif.). The reverse transcription was performed with reagents and kits from Invitrogen. Quantification of mRNA expression was performed using the Taqman gene expression assays and the following primers (VEGFa, Hs00173626_m1; IL-1β, Hs01555413_m1; IL-6, Hs00174131_m1; IL-8, Hs00174103_m1; IκBα, Hs00153283_m1; GRP78, Hs99999174_m1; CHOP, Hs01090850_m1; NOX2, Hs00166163_m1; NOX4, Hs01558199_m1; SCD, Hs00748952 s1; TNF-α, Hs00174128_m1; TGF-β1, Hs00998133_m1; GAPD, 4352934e). GAPD expression was used as an endogenous standard. All qRT-PCR experiments were measured in triplicates in an ABI 7500 Real-Time PCR Instrument (Applied Biosystems, Foster City, Calif.). The results of each treatment were normalized and presented in percentage relative to the vehicle-only control.

ELISA Assays

The levels of secreted VEGF, IL-6, IL-8, and TNF-α in conditioned medium of ARPE-19 cell cultures were measured 48 hr after treatments of 6 μM 7KCh and 1 μM fatty acids using the Quantkine ELISA kits from R&D systems (Minneapolis, Minn.). The protein levels were measured in triplicates. The ELISA results were quantified using an Envision multilable plate reader (PerkinElmer, Covina, Calif.) and presented in percentage relative to the vehicle-only control.

Immunoblots

Lysis of ARPE-19 cells was performed using MPER buffer solution (Thermo Fisher Scientific) containing Complete Protease Inhibitor Cocktail (Roche Diagnostics). A total of 10 μg protein samples of the cell lysate were separated by SDS-PAGE on 10% Bis-Tris gels (Invitrogen). The gels were blotted on to nitrocellulose membranes (Invitrogen). The proteins were probed with primary antibodies for CHOP (1:1000 dilution), GRP78 (1:1000), or GAPDH (1:2000) at 4° C. overnight. The membranes were then further incubated with anti-rabbit IgG, HRP-linked antibodies (1:2000 dilution) at room temperature for 1 hr. The membranes were developed using Chemiluminescent Substrate (Thermo Fisher Scientific) and visualized using a Kodak X-OMAT 2000A processor (Carestream Health, Rochester, N.Y.).

Analysis of 7KCh Levels in Photocoagulated Tissues by LCMS

Rats were anesthetized with an intraperitoneal injection of a 40 to 80 mg/kg ketamine (Fort Dodge Animal Health, Fort Dodge Iowa) and 10 to 12 mg/kg xylazine (Ben Venue Laboratories, Bedford Ohio) mixture. A drop of 0.5% proparacaine was applied topically followed by pupil dilation using a mixture of 1% tropicamide and 2.5% phenylephrine (Alcon, Fort Worth Tex.). Hot pads maintained the body temperature of rats placing in front of a slit lamp.

To evaluate the level of 7KCh in tissue after photocoagulation, 8 or 32 laser burns (OcuLight® 532 nm laser system (Iridex, Mountain View Calif.) with a 5.4 mm contact fundus laser lens (Ocular Instruments, Bellevue Wash.), 50 μm spot size, 0.1 second duration, 80-90 mW) were made in each eye surrounding the optic nerve. The eyes were removed at 6, 24 and 48 hr post laser treatment and the neural retina (NR) was separated from the RPE/choroid (PEC) and snap-frozen in dry ice. Each sample contained 2 retinas or PEC and each time point was repeated 3 times. Retinas with no laser treatment were used as controls.

To each sample 100 nmoles of deuterated cholesterol (D7-Ch) were added then lyophilized. To the dry samples 1 ml of dry ethanol was added and homogenized in a tissue grinder. The insoluble material was removed by centrifugation and the ethanol placed in an HPLC vial and dried under a nitrogen stream. Each vial was then reconstituted with 100 ul of ethanol. The 7KCh, cholesterol (Ch), and the 7-ketocholesterol fatty acid esters (7KFAEs) were separated by HPLC and identified and quantified by MS.

The analyses were performed using an Agilent 1200 series HPLC (Santa Clara, Calif.) equipped with a capillary pump, a column heater and an autosampler and connected to a Waters/Micromass QTOF micro (Milford, Mass.) equipped with an APCi probe. A Varian (Agilent) XRs C8 column (2×100 mm) running a binary gradient at 0.1 ml/min was used to separate the 7KCh, Ch, and 7KFAEs esters. The initial condition were 25% water, 75% acetonitrile 0.1% formic acid and the gradient was completed in 10 min reaching 100% methanol, 0.1% formic acid. The 100% methanol was sustained for an additional 25 min then the column was re-equilibrated to initial condition for an additional 10 min. The chromatography was performed at 60° C. Each sample (5 μl) was injected twice.

7KCh, Ch, and 7KFAEs were quantified using the various ions listed below. Standard curves were prepared for each of the compounds of interest, 7KCh, D7-Ch, Ch, D7-Ch and 7K-18:1 ester.

|  | ion | RT | m/z |
|---|---|---|---|
| 7KCh | M + H | 15.8 | 401 |
| D7-7K | M + H | 15.7 | 408 |
| Ch | M − OH | 19.7 | 369 |
| D7-Ch | M − OH | 19.65 | 376 |
| 7K-18:1 | M − FA | 32.4 | 383 |

The various ions were quantified by peak area integration. The formation of D7-7K during the extraction process was usually nil for most samples. In the cases where D7-7K was formed it was subtracted from the 7KCh amount based on % formation. The levels of 7KCh were reported as pmol per namol of Ch. Since standards for all of the various 7KFAEs found were lacking, the response of 7K-18:1 was used to quantify all of the esters.

Laser-Induced Choroidal Neovascularization (CNV) Model

Rats were anesthetized and prepared as described above. To evaluate the in vivo antagonist effect of sterculic acid to 7KCh, four laser burns (50 µm spot size, 0.1 second duration, 80-90 mW) were made in each eye surrounding the optic nerve. Laser breakage of Bruch's membrane was observed by the formation of a bubble. The laser-induced CNV lesions were evaluated 7 days after laser treatment.

Intravitreal Injections of Sterculic Acid and Oleic Acid

The intravitreal injection was performed at 24 or 48 hr after laser treatment. After anesthesia and pupil dilation, a 33G needle attached to a Hamilton syringe to pierce the sclera at the level of the pars plana was used under microscope visualization. The needle was introduced parallel to the retina to avoid damaging the lens. Sterilized 10% DMSO/PBS containing 1 mM sterculic acid, or 1 mM oleic acid (1 µl) was injected into the vitreous cavity. This was followed by topically applied Neomycin and polymyxin B sulfates and bacitratin zinc ophthalmic ointment USP (Bausch & Lomb, Rochester N.Y.). Seven days after laser treatment, all animals were euthanized for CNV lesion evaluation. At least 45 samples of each treatment were pooled for the evaluation.

Topical Delivery of Sterculic Acid and Oleic Acid

Sterculic acid and oleic acid were dissolved in 10% DMSO/PBS at neutral pH and used directly as eye drop solutions. Immediately after laser treatment, rats were administered with solutions containing sterilized 10% DMSO/PBS, 1 mM sterculic acid, or 1 mM oleic acid one drop/day; or with solutions containing sterilized 10% DMSO/PBS, 0.1 mM, 1 mM, or 10 mM sterculic acid three drops/day, for 6 consecutive days. Afterwards, all animals were euthanized for CNV lesion evaluation. At least 38 lesions for of each treatment were pooled for the evaluation.

CNV Lesion Volume Evaluation

Animals were euthanized by $CO_2$ exposure. The rat eyes were enucleated and flat-mounted, as previously described.[33] Neovessels were visualized by labeling the endothelial cells in the RPE/choroid flat mounts using Alexa Fluor 568-isolectin $IB_4$ (Invitrogen). Multiplane z-stacks of the neovessels were collected with an epifluorescent microscope (Zeiss Apo-Tome, Thornwood N.Y.). The neovessel volume was determined using a high-performance 3D imaging software (Volocity; Perkin Elmer, Wellesley, Mass.) as previously described[33,34].

Statistical Analysis

Statistical comparisons between groups were performed using two-tailed Student's t-test.

Results

Unsaturated Fatty Acids are Antagonists to 7KCh-Induced Cytotoxicity

Unsaturated fatty acids have been previously shown to have anti-inflammatory effects and seem to provide beneficial effect in atherosclerosis. In order to determine if PUFAs were antagonist to 7KCh-mediated cytotoxicity, unsaturated fatty acids including ω-3 (18:3 and 22:6), ω-6 (18:2 and 20:4), and ω-9 (18:1, 19Δ:0, 19Δ:1) were tested. Stearic acid (18:0) which is fully saturated fatty acid was used as control (Table 3).

TABLE 3

Fatty acids protect ARPE-19 cells against 7KCh-mediated cytotoxicity*

| FATTY ACID | TYPE | CONC. (µM) |
|---|---|---|
| α-Linolenic acid (18:3) | ω-3 | 5 |
| Docosahexaenoic acid (22:6) | ω-3 | 5 |
| Linoleic acid (18:2) | ω-6 | 5 |
| Arachidonic acid (20:4) | ω-6 | 10 |
| Sterculic acid (19Δ:1) | ω-9 | 1 |
| Dihydrosterculic acid (19Δ:0) | ω-9 | 10 |
| Oleic acid (18:1) | ω-9 | 10 |
| Stearic acid (18:0) | x | x |

*ARPE-19 cells were treated with 12 µM 7KCh for 24 hr. The results were concluded after three independent experiments with quadruplicate measurements in each experiment.

Figure 12:
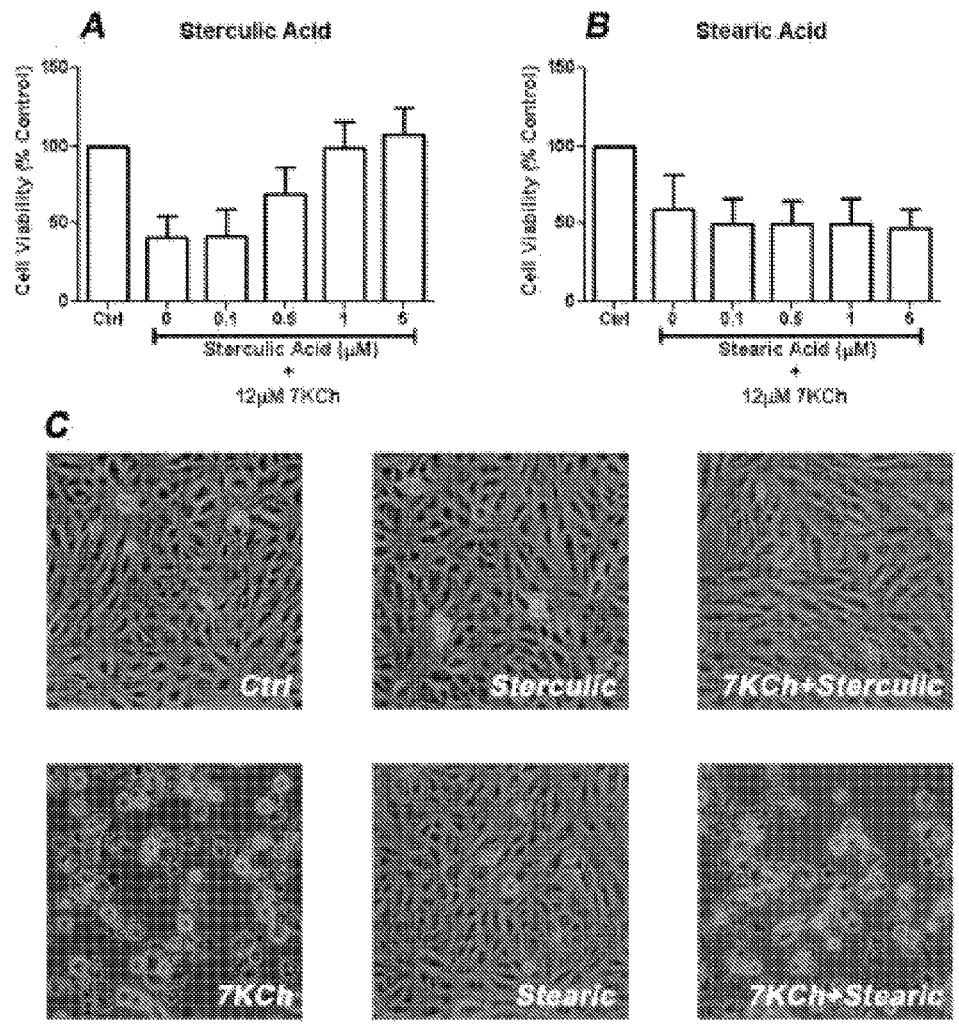
FIGS. 12A-12C depict ARPE-19 cell viability in response to 12 μM 7KCh with or without 0.1-5 μM (A) sterculic acid and (B) stearic acid after 24 hr treatments. Error bars indicate the standard deviations. n=3-5. Two-tailed Student's t-test. (C) Representative images of changes in cell morphology in response to 12 μM 7KCh with or without 1 μM sterculic acid and stearic acid after 24 hr treatments.

The lowest effective concentrations of fatty acids that offset the 7KCh-mediated cell death were determined. ARPE-19 cells were treated with 12 µM 7KCh ($LD_{50}$) with or without increasing concentrations of fatty acids (0.1, 0.5, 1, 5 and 10 µM) for 24 hr. Table 3 lists the lowest concentrations of these fatty acids required to maintain full cell viability against 12 µM 7KCh treatment. All unsaturated fatty acids protected against 7KCh-induced cell death. Among the unsaturated fatty acids, sterculic acid was by far the most effective compound. At 0.5 µM sterculic acid significantly increased cell viability (FIG. 12A) and at 1 µM sterculic acid completely offset the cell death induced by 7KCh. DHA, α-linolenic, and linoleic acid prevented 7KCh-mediated cell death at 5 µM but the rest of unsaturated fatty acids and dihydrosterculic acid required 10 µM to be protective. Stearic acid (18:0) did not demonstrate any protective effect against 7KCh-mediated cell death (FIG. 12B). The difference between stearic and dihydrosterculic (19Δ:0) suggests the cyclopropane group at C-9 is a critical structure. To demonstrate the morphological effects on the cells, representative images of the treated cultures are shown in FIG. 12C. The images demonstrate that 1 µM sterculic acid effectively protect the cells from a 12 µM dose of 7KCh while the stearic acid control had no effect.

Effect of Fatty Acids on 7KCh-Mediated Inflammation

Figure 13:
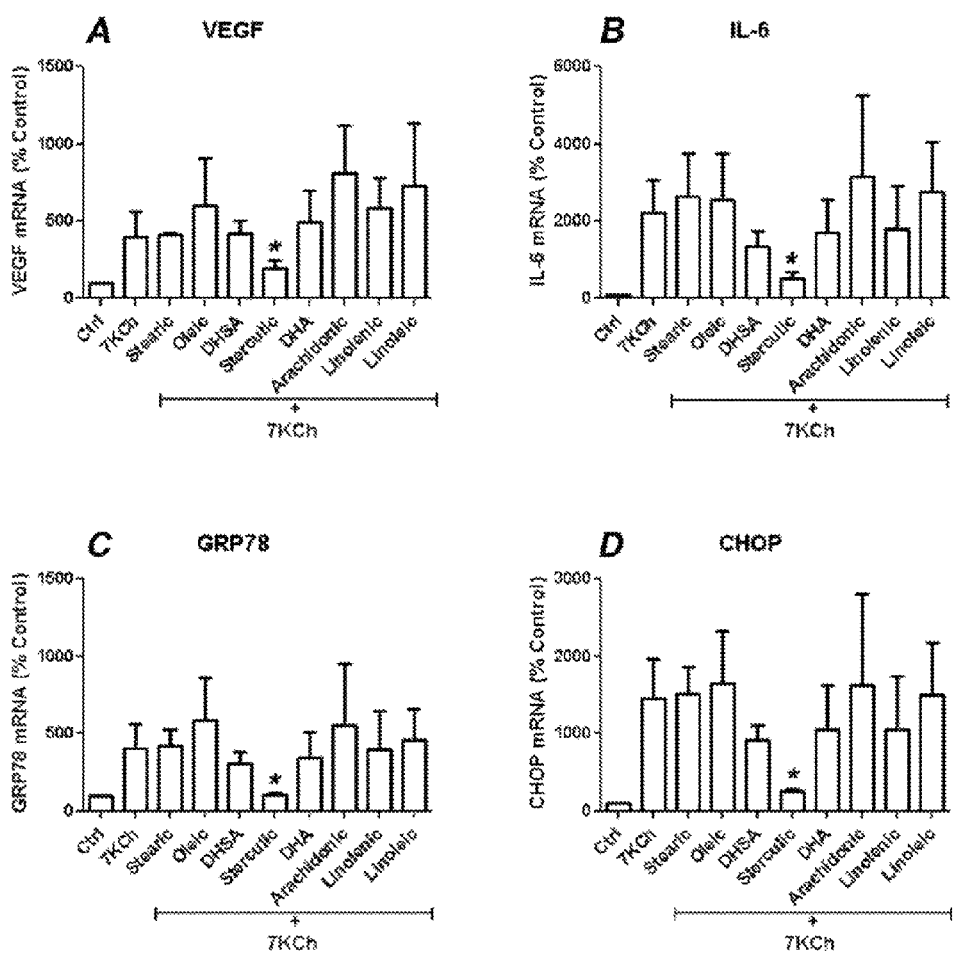
FIGS. 13A-13D depict mRNA expressions of (A) VEGF, (B) IL-6, (C) GRP78, and (D) CHOP in response to 8 μM 7KCh with or without 1 μM long-chain fatty acids. Error bars indicate the standard deviations. *p<0.05 comparing to 7KCh, n=3. Two-tailed Student's t-test.

Since unsaturated fatty acids demonstrated a protective effect against cell viability, the ability of these fatty acids to antagonize the 7KCh-mediated induction of inflammatory cytokines and ER stress markers at 1 µM was tested. Stearic acid was again used as a negative control. ARPE-19 cells treated with 8 µM 7KCh for 24 hr and the mRNA expression of VEGF, IL-6, GRP78, and CHOP were measured by qRT-PCR (FIG. 13). At 1 µM, only sterculic acid demonstrated a complete inhibition of the 7KCh-mediated mRNA induction. 7KCh increased the expression of VEGF, IL-6, GRP78, and CHOP mRNA, 4-, 22-, 4-, and 15-fold, respectively. Simultaneous treatment with 7KCh and sterculic acid reduced the mRNA expressions of VEGF (FIG. 13A), IL-6 (FIG. 13B), GRP78 (FIG. 13C), and CHOP (FIG. 13D) to basal levels.

Treatments with 1 µM DHSA (19Δ:0), DHA (22:6), and α-linolenic (18:3) acid were somewhat effective at reducing IL-6, GRP78 and CHOP but essentially ineffective against VEGF (FIG. 13). The other fatty acids—stearic (18:0), Oleic (18:1), linoleic (18:2) and arachidonic (20:4)—were either ineffective or enhanced the 7KCh-mediated inflammatory response (FIG. 13).

The Antagonist Effect of Sterculic Acid to 7KCh-Mediated Inflammation

Figure 14:
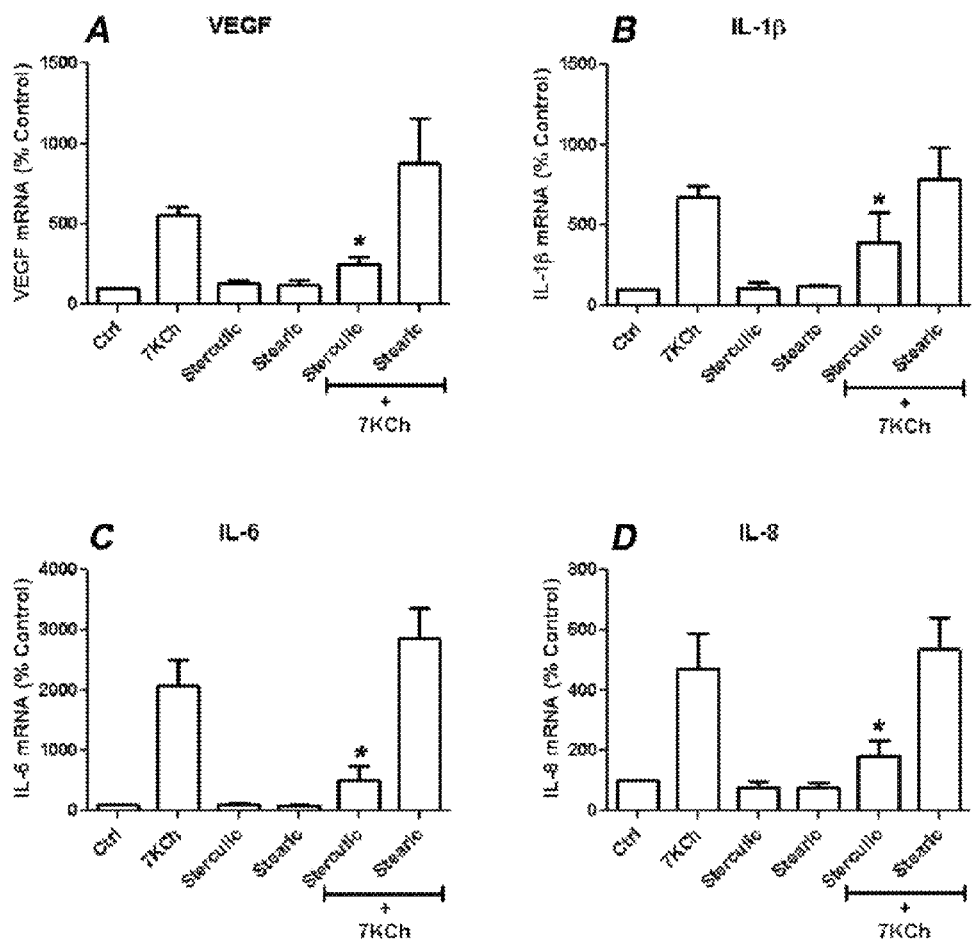
FIGS. 14A-14D depict mRNA expressions of (A) VEGF, (B) IL-1b, (C) IL-6, and (D) IL-8 in response to 8 μM 7KCh, 1 μM sterculic acid, 1 μM stearic acid, or the combinations of 7KCh with either sterculic acid or stearic acid. Error bars indicate the standard deviations. *p<0.05 comparing to 7KCh, n=4. Two-tailed Student's t-test.
Figure 15:
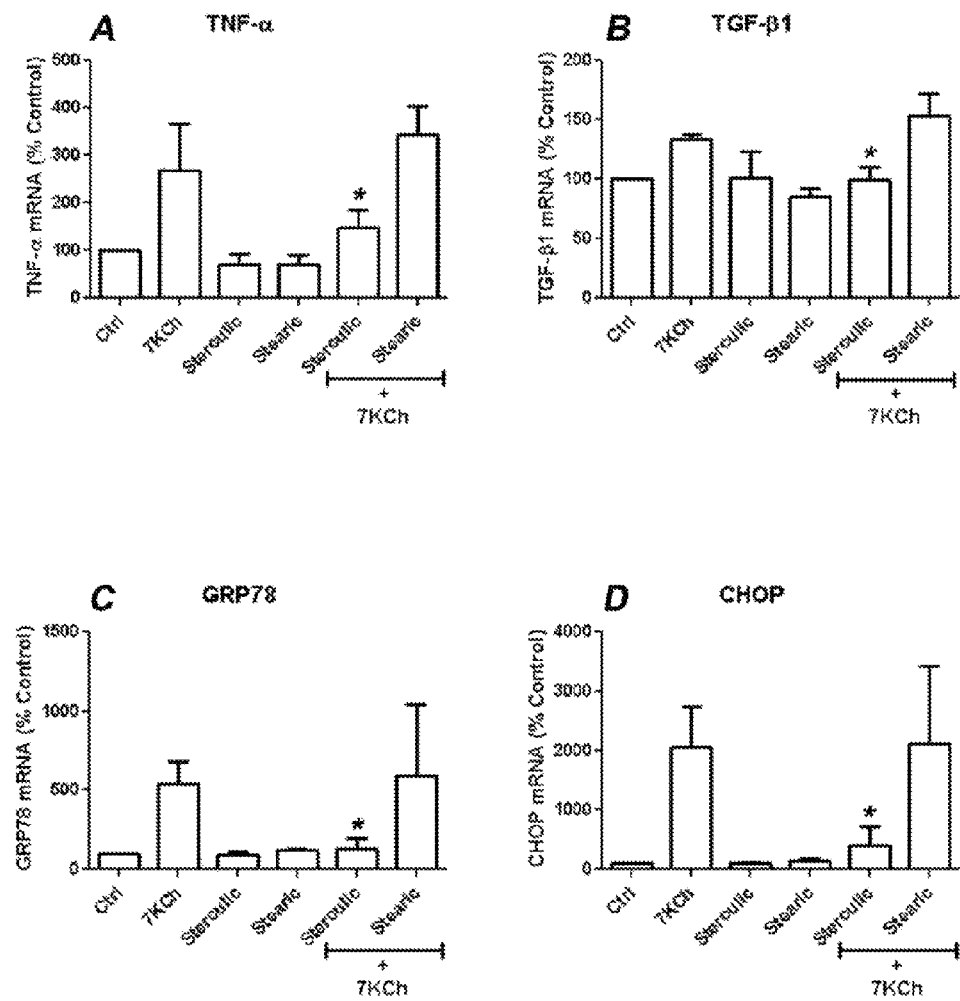
FIGS. 15A-15D depict mRNA expressions of (A) TNF-α, (B) TGF-β1, (C) GRP78, and (D) CHOP in response to 8 μM 7KCh, 1 μM sterculic acid, 1 μM stearic acid, or the combinations of 7KCh with either sterculic acid or stearic acid. Error bars indicate the standard deviations. *p<0.05 comparing to 7KCh, n=3-4. Two-tailed Student's t-test.

Because sterculic acid appears to be the most effective antagonist to 7KCh-mediated expression of VEGF, IL-6, GRP78, and CHOP, analyses to IL-1β and IL-8 (FIG. 14) and TNFα and TGFβ1 (FIG. 15) was expanded. VEGF, IL-6, GRP78, and CHOP were included in this series of experiments for direct comparison (FIGS. 14, 15). Stearic acid was used as a negative control. Sterculic acid attenuated the induction of VEGF, from 5.5 to 2.5-fold (FIG. 14A); IL-1β, from 6.7 to 3.9-fold (FIG. 14B); IL-6, from 21 to 5.1-fold (FIG. 14C); IL-8, from 4.7 to 1.8-fold (FIG. 14D). Sterculic acid also attenuated the induction of TNF-α, from 2.7 to 1.5-fold (FIG. 15A); TGF-β1, from 1.3 to 1-fold (FIG. 15B) and the ER stress markers GRP78, from 5.4 to 1.3-fold (FIG. 15C); and CHOP, from 12 to 4.1-fold (FIG. 15D). Stearic acid did not show any antagonistic effect but seemed to enhanced the expression of VEGF (from 5.5 to 8.8-fold) and IL-6 (from 21 to 29-fold). Sterculic acid or stearic acid alone had no effect on the mRNA expression of these cytokines (FIGS. 14, 15).

Figure 16:
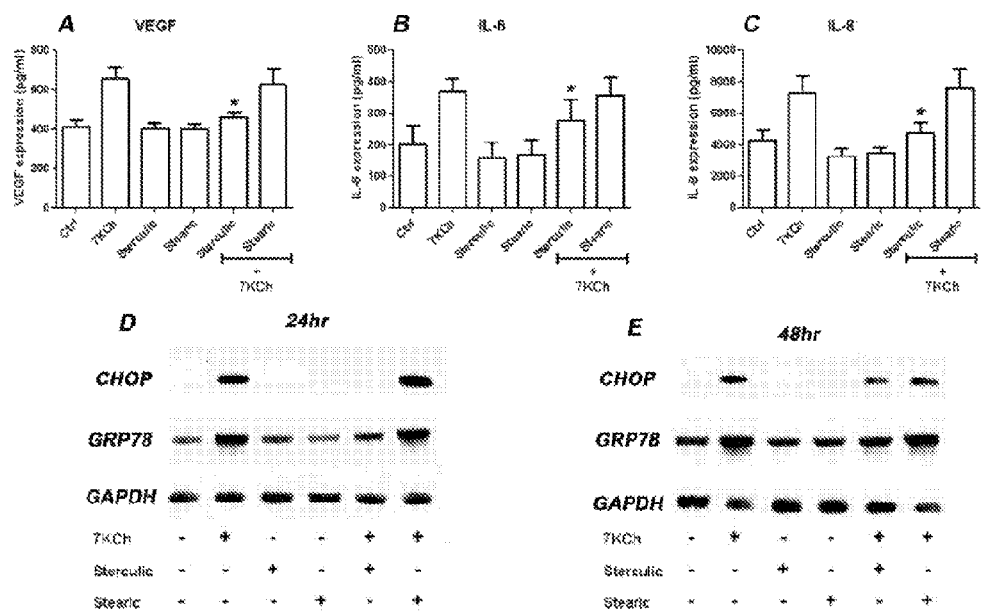
FIGS. 16A-16E depict the secreted protein levels of (A) VEGF, (B) IL-6, and (C) IL-8 were measure by ELISA 48 hr after treatment with 6 μM 7KCh, 1 μM sterculic acid, 1 μM stearic acid, or the combinations of 7KCh with either sterculic acid or stearic acid. Error bars indicate the standard deviations. *p<0.05 comparing to 7KCh, n=3. Two-tailed Student's t-test. The expressions of GRP78 and CHOP were shown by immunoblots (D) 24 hr or (E) 48 hr after treatment with 8 μM 7KCh, 1 μM sterculic acid, 1 μM stearic acid, or the combinations of 7KCh with either sterculic acid or stearic acid.

Since mRNA expression does not necessarily correlate with protein expression, the secreted protein levels of VEGF, IL-6, IL-8, and TNF-α and the intracellular protein levels of CHOP and GRP78 was examined (FIG. 16). ARPE-19 cells were treated with 7KCh with or without sterculic and stearic acid. The secreted VEGF, IL-6, and IL-8 protein levels were measured by ELISA (FIG. 16A-C). These experiments demonstrated that sterculic acid reduced the secreted levels of these proteins and followed a similar trend as the mRNA expression. The 7KCh treatments increased the protein expressions of VEGF 1.6-fold, IL-6 1.8-fold, and IL-8 1.7-fold while sterculic acid reduced the expressions of VEGF, 1.1-fold; IL-6, 1.4-fold; IL-8, 1.1-fold. Stearic again had no measurable effect. The immunoblots of ER stress markers CHOP and GRP78 also showed a similar trend as the mRNA expression (FIG. 16 D,E). The 24 hr 7KCh treatment induced CHOP and GRP78 protein expression but these inductions were completely inhibited by sterculic acid. Stearic acid again had no effect (FIG. 20D,E). The inhibitory effect of sterculic acid on CHOP and GRP78 protein expression seems to decrease after 48 hr (FIG. 16E). Comparing to vehicle-only control, the expression of CHOP and GRP78 did not change when the cells were treated with fatty acids alone. Secreted TNF-α protein expression was not detected (data not shown).

Sterculic Acid is not Antagonistic to TNF-α

Figure 17:
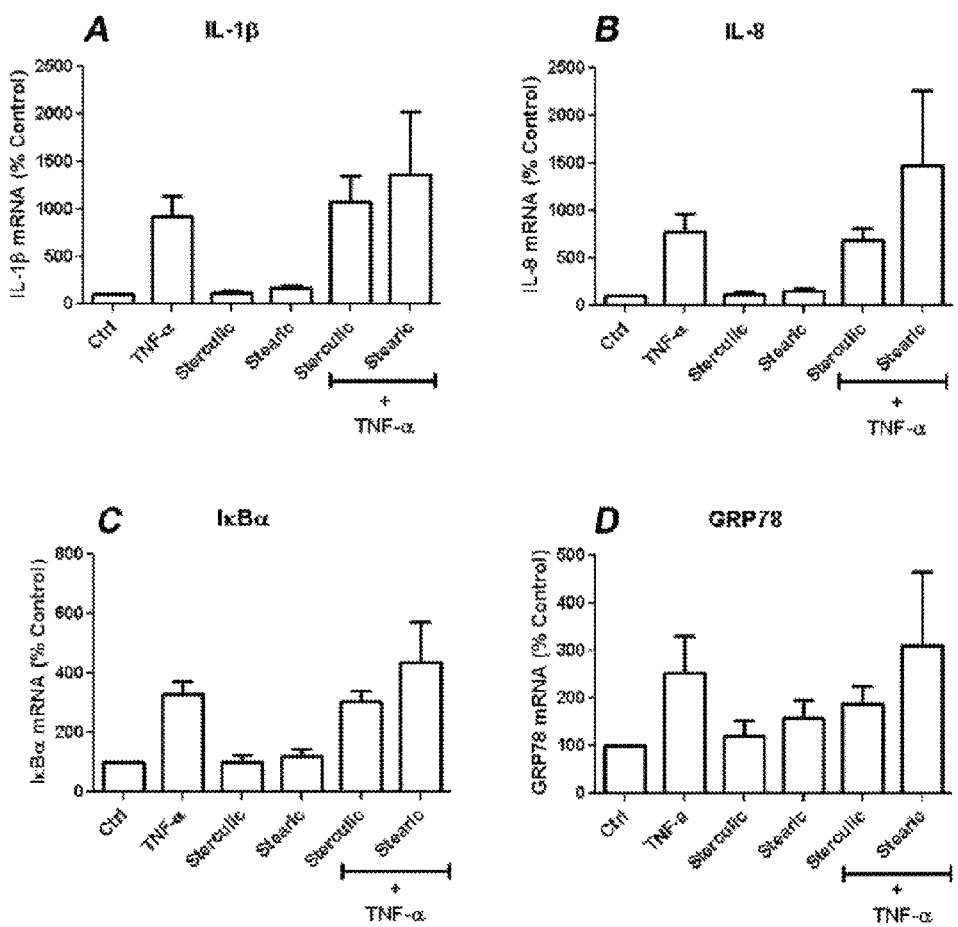
FIGS. 17A-17D depict the mRNA expressions of (A) IL-1β, (B) IL-8, (C) IκBα, and (D) GRP78 in response to 2 ng/ml TNF-α, 1 μM sterculic acid, 1 μM stearic acid, or the combinations of TNF-α with either sterculic acid or stearic acid. n=3. Error bars indicate the standard deviations.

In order to understand whether the anti-inflammatory effect of sterculic acid is specific to the 7KCh or a more generalized effect, its effects on TNF-α treated cells was examined. TNF-α is a common pro-inflammatory cytokine that induces inflammation via several TNF receptors. ARPE-19 cells were incubated in 2 ng/ml TNF-α with or without 1 μM sterculic acid and stearic acid for 24 hr. The TNF-α treatment significantly induced the mRNA expressions of IL-1β (9-fold), IL-8 (8-fold), IκBα (3-fold), and GRP78 (2.5-fold) but not VEGF, IL-6, and CHOP (data not shown). Sterculic acid did not show any antagonist effect to the cytokine inductions by TNF-α but did have a small measurable effect on GRP78 (FIG. 17D). Stearic acid seemed to enhance the TNF-α induction of the cytokines Sterculic acid also failed to antagonize the effects of TNF-α at 5 μM (data not shown).

7KCh-Mediated Inflammation and SCD Inhibition

It has been reported that ceramide plays an important role in 7KCh-mediated cell death. Sterculic acid is known to inhibit the expression of stearoyl-CoA desaturase (SCD), which in turn inhibits the production of ceramide. As such, SCD inhibition may be responsible for the protective effect of sterculic acid to 7KCh-mediated cytotoxicity.

Figure 18:
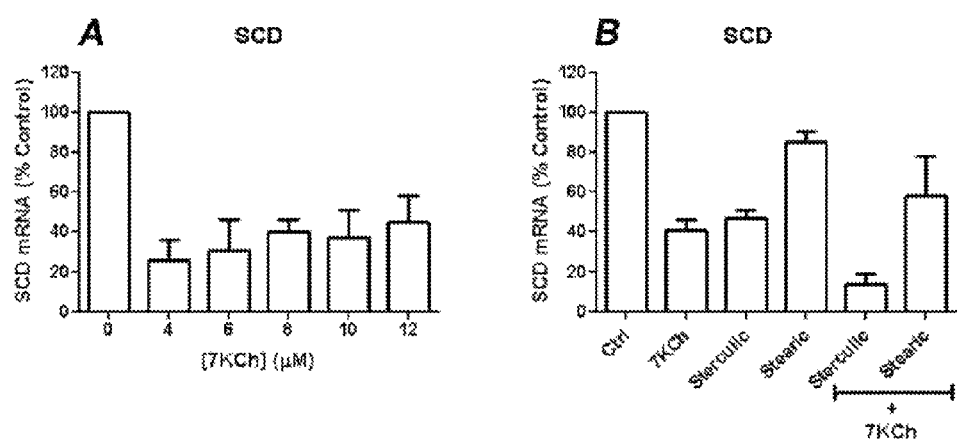
FIGS. 18A and 18B depict (A) Dose response of SCD mRNA inductions by 0-12 μM 7KCh after 24 hr treatments. (B) The mRNA expressions of SCD in response to 8 μM 7KCh, 1 μM sterculic acid, 1 μM stearic acid, or the combinations of 7KCh with either sterculic acid or stearic acid. Error bars indicate the standard deviations. n=4.

To determine the effect of 7KCh on SCD expression ARPE-19 cells were incubated with 4 μM 7KCh for 24 hr. 7KCh suppressed SCD mRNA expression by approximately 60-70% (FIG. 18A). Higher concentrations of 7KCh did not further suppress SCD mRNA expression. Sterculic acid (1 μM), as expected, inhibited SCD expression similarly to 8 μM 7KCh (FIG. 18B). Treatment of the cells with 8 μM 7KCh and 1 μM sterculic acid further suppress SCD expression to 86% (FIG. 18B). The significant inhibition of SCD expression by 7KCh suggests that the protective effects of sterculic are likely unrelated to SCD inhibition. This is the only instance where 7KCh and sterculic acid worked synergistically rather than antagonistically.

REFERENCES

D. E. Khoo et al., Manipulation of body fat composition with sterculic acid can inhibit mammary carcinomas in vivo. Br. J. Cancer. 1991 January; 63(1): 97-101.

U.S. Pat. No. 4,778,630

Jeffcoat, R. et al., Studies on the Inhibition of the Desaturases by Cyclopropenoid Fatty Acids, Lipids, vol. 12, no. 6, 480-485.

Zoeller et al., The importance of the stearoyl-CoA-desaturase system in octadecenoate metabolism in the Morris hepatoma 7288C, Biochimica et Biophysica Acta 845 (1985) 380-388.

Fermor, B. F., et al., Fatty Acid Composition of Normal and Malignant Cells and Cytotoxicity of Stearic, Oleic and Sterculic Acids in vitro, Eur. J. Cancer, vol. 28A, No. 67, pp 1143-1147, 1992.

Khoo, D. E., et al., Manipulation of body fat composition with sterculic acid can inhibit mammary carcinomas in vivo, Br. J. Cancer (1991), 63, 97-101.

Gomez, F. E., et al., Effects of sterculic acid on stearoyl-CoA desaturase in differentiating 3T3-L1 adipocytes, Biochemical and Biophysical Research Communications 300 (2003) 316-326.S Curcio, C. A., Johnson, M., Huang, J. D. & Rudolf, M. Aging, age-related macular degeneration, and the response-to-retention of apolipoprotein B-containing lipoproteins. *Prog Retin Eye Res* 28, 393-422 (2009).

Sevitt, S. Platelets and foam cells in the evolution of atherosclerosis. Histological and immunohistological studies of human lesions. *Atherosclerosis* 61, 107-115 (1986).

Guyton, J. R. & Klemp, K. F. Development of the lipid-rich core in human atherosclerosis. *Arterioscler Thromb Vasc Biol* 16, 4-11 (1996).

Rodriguez, I. R. & Larrayoz, I. M. Cholesterol oxidation in the retina: implications of 7KCh formation in chronic inflammation and age-related macular degeneration. *J Lipid Res* 51, 2847-2862 (2010).

Yamada, Y. et al. Oxidized low density lipoproteins induce a pathologic response by retinal pigmented epithelial cells. *J Neurochem* 105, 1187-1197 (2008).

Matsuura, E., Kobayashi, K., Tabuchi, M. & Lopez, L. R. Oxidative modification of low-density lipoprotein and immune regulation of atherosclerosis. *Prog Lipid Res* 45, 466-486 (2006).

Kita, T. et al. The role of oxidized low density lipoprotein in the pathogenesis of atherosclerosis. *Eur Heart J* 11 Suppl E, 122-127 (1990).

Jialal, I. & Devaraj, S. The role of oxidized low density lipoprotein in atherogenesis. *J Nutr* 126, 1053S-1057S (1996).

Hughes, H., Mathews, B., Lenz, M. L. & Guyton, J. R. Cytotoxicity of oxidized LDL to porcine aortic smooth muscle cells is associated with the oxysterols 7-ketocholesterol and 7-hydroxycholesterol. *Arterioscler Thromb* 14, 1177-1185 (1994).

Rodriguez, I. R., Alam, S. & Lee, J. W. Cytotoxicity of oxidized low-density lipoprotein in cultured RPE cells is dependent on the formation of 7-ketocholesterol. *Invest Ophthalmol Vis Sci* 45, 2830-2837 (2004).

Nishio, E., Arimura, S. & Watanabe, Y. Oxidized LDL induces apoptosis in cultured smooth muscle cells: a possible role for 7-ketocholesterol. *Biochem Biophys Res Commun* 223, 413-418 (1996).

Larrayoz, I. M., Huang, J. D., Lee, J. W., Pascual, I. & Rodriguez, I. R. 7-ketocholesterol-induced inflammation: involvement of multiple kinase signaling pathways via NFkappaB but independently of reactive oxygen species formation. *Invest Ophthalmol Vis Sci* 51, 4942-4955 (2010).

Li, G., Scull, C., Ozcan, L. & Tabas, I. NADPH oxidase links endoplasmic reticulum stress, oxidative stress, and PKR activation to induce apoptosis. *J Cell Biol* 191, 1113-1125 (2010).

Dulak, J. et al. Vascular endothelial growth factor synthesis in vascular smooth muscle cells is enhanced by 7-ketocholesterol and lysophosphatidylcholine independently of their effect on nitric oxide generation. *Atherosclerosis* 159, 325-332 (2001).

Lizard, G. et al. Induction of apoptosis and of interleukin-1beta secretion by 7beta-hydroxycholesterol and 7-ketocholesterol: partial inhibition by Bcl-2 overexpression. *FEBS Lett* 419, 276-280 (1997).

Leonarduzzi, G. et al. Up-regulation of the fibrogenic cytokine TGF-beta1 by oxysterols: a mechanistic link between cholesterol and atherosclerosis. *Faseb J* 15, 1619-1621 (2001).

Brown, A. J., Leong, S. L., Dean, R. T. & Jessup, W. 7-Hydroperoxycholesterol and its products in oxidized low density lipoprotein and human atherosclerotic plaque. *J Lipid Res* 38, 1730-1745 (1997).

Moreira, E. F., Larrayoz, I. M., Lee, J. W. & Rodriguez, I. R. 7-Ketocholesterol is present in lipid deposits in the primate retina: potential implication in the induction of VEGF and CNV formation. *Invest Ophthalmol Vis Sci* 50, 523-532 (2009).

Garcia-Cruset, S., Carpenter, K. L., Guardiola, F., Stein, B. K. & Mitchinson, M. J. Oxysterol profiles of normal human arteries, fatty streaks and advanced lesions. *Free Radic Res* 35, 31-41 (2001).

Sottero, B., Gamba, P., Gargiulo, S., Leonarduzzi, G. & Poli, G. Cholesterol oxidation products and disease: an emerging topic of interest in medicinal chemistry. *Curr Med Chem* 16, 685-705 (2009).

Calder, P. C. n-3 polyunsaturated fatty acids, inflammation, and inflammatory diseases. *Am J Clin Nutr* 83, 1505S-1519S (2006).

Doshi, M. et al. Effect of dietary enrichment with n-3 polyunsaturated fatty acids (PUFA) or n-9 PUFA on arachidonate metabolism in vivo and experimentally induced inflammation in mice. *Biol Pharm Bull* 27, 319-323 (2004).

Bousserouel, S., Brouillet, A., Bereziat, G., Raymondjean, M. & Andreani, M. Different effects of n-6 and n-3 polyunsaturated fatty acids on the activation of rat smooth muscle cells by interleukin-1 beta. *J Lipid Res* 44, 601-611 (2003).

Tull, S. P. et al. Omega-3 Fatty acids and inflammation: novel interactions reveal a new step in neutrophil recruitment. *PLoS Biol* 7, e1000177 (2009).

SanGiovanni, J. P. et al. The relationship of dietary omega-3 long-chain polyunsaturated fatty acid intake with incident age-related macular degeneration: AREDS report no. 23. *Arch Ophthalmol* 126, 1274-1279 (2008).

Chong, E. W., Kreis, A. J., Wong, T. Y., Simpson, J. A. & Guymer, R. H. Dietary omega-3 fatty acid and fish intake in the primary prevention of age-related macular degeneration: a systematic review and meta-analysis. *Arch Ophthalmol* 126, 826-833 (2008).

Ramsden, C. E., Hibbeln, J. R., Majchrzak, S. F. & Davis, J. M. n-6 fatty acid-specific and mixed polyunsaturate dietary interventions have different effects on CHD risk: a meta-analysis of randomised controlled trials. *Br J Nutr* 104, 1586-1600 (2010).

Psota, T. L., Gebauer, S. K. & Kris-Etherton, P. Dietary omega-3 fatty acid intake and cardiovascular risk. *Am J Cardiol* 98, 3i-18i (2006).

He, K. et al. Associations of dietary long-chain n-3 polyunsaturated fatty acids and fish with biomarkers of inflammation and endothelial activation (from the Multi-Ethnic Study of Atherosclerosis [MESA]). *Am J Cardiol* 103, 1238-1243 (2009).

Kamei, M. et al. Scavenger receptors for oxidized lipoprotein in age-related macular degeneration. *Invest Ophthalmol Vis Sci* 48, 1801-1807 (2007).

Chen, H. et al. EPA and DHA attenuate ox-LDL-induced expression of adhesion molecules in human coronary artery endothelial cells via protein kinase B pathway. *J Mol Cell Cardiol* 35, 769-775 (2003).

Bao, X., Katz, S., Pollard, M. & Ohlrogge, J. Carbocyclic fatty acids in plants: biochemical and molecular genetic characterization of cyclopropane fatty acid synthesis of Sterculiafoetida. *Proc Natl Acad Sci USA* 99, 7172-7177 (2002).

Campos, M., Amaral, J., Becerra, S. P. & Fariss, R. N. A novel imaging technique for experimental choroidal neovascularization. *Invest Ophthalmol Vis Sci* 47, 5163-5170 (2006).

Dobi, E. T., Puliafito, C. A. & Destro, M. A new model of experimental choroidal neovascularization in the rat. *Arch Ophthalmol* 107, 264-269 (1989).

Pahl, H. L. Activators and target genes of Rel/NF-kappaB transcription factors. *Oncogene* 18, 6853-6866 (1999).

Li, Q. & Verma, I. M. NF-kappaB regulation in the immune system. *Nature reviews* 2, 725-734 (2002).

Gilmore, T. D. Introduction to NF-kappaB: players, pathways, perspectives. *Oncogene* 25, 6680-6684 (2006).

Vallabhapurapu, S. & Karin, M. Regulation and function of NF-kappaB transcription factors in the immune system. *Annual review of immunology* 27, 693-733 (2009).

Velasco, M., Diaz-Guerra, M. J., Martin-Sanz, P., Alvarez, A. & Bosca, L. Rapid Up-regulation of IkappaBbeta and abrogation of NF-kappaB activity in peritoneal macrophages stimulated with lipopolysaccharide. *J Biol Chem* 272, 23025-23030 (1997).

Wajant, H., Pfizenmaier, K. & Scheurich, P. Tumor necrosis factor signaling. *Cell Death Differ* 10, 45-65 (2003).

Miguet, C. et al. Ceramide generation occurring during 7beta-hydroxycholesterol- and 7-ketocholesterol-induced apoptosis is caspase independent and is not required to trigger cell death. *Cell Death Differ* 8, 83-99 (2001).

Ntambi, J. M. Regulation of stearoyl-CoA desaturase by polyunsaturated fatty acids and cholesterol. *J Lipid Res* 40, 1549-1558 (1999).

James, A. T., Harris, P. & Bezard, J. The inhibition of unsaturated fatty acid biosynthesis in plants by sterculic acid. *Eur J Biochem* 3, 318-325 (1968).

Dobrzyn, A. et al. Stearoyl-CoA desaturase-1 deficiency reduces ceramide synthesis by downregulating serine palmitoyltransferase and increasing beta-oxidation in skeletal muscle. *Am J Physiol Endocrinol Metab* 288, E599-607 (2005).

Rodriguez, I. R. & Fliesler, S. J. Photodamage generates 7-keto- and 7-hydroxycholesterol in the rat retina via a free radical-mediated mechanism. *Photochem Photobiol* 85, 1116-1125 (2009).

Duran, M. J. et al. 7-ketocholesterol inhibits Na,K-ATPase activity by decreasing expression of its alpha1-subunit and membrane fluidity in human endothelial cells. *Cell Mol Biol (Noisy-le-grand)* 56 Suppl, OL1434-1441 (2010).

Luthra, S. et al. 7-Ketocholesterol activates caspases-3/7, -8, and -12 in human microvascular endothelial cells in vitro. *Microvasc Res* 75, 343-350 (2008).

Enoch, H. G., Catala, A. & Strittmatter, P. Mechanism of rat liver microsomal stearyl-CoA desaturase. Studies of the substrate specificity, enzyme-substrate interactions, and the function of lipid. *J Biol Chem* 251, 5095-5103 (1976).

Harvey, K. A. et al. Long-chain saturated fatty acids induce pro-inflammatory responses and impact endothelial cell growth. *Clin Nutr* 29, 492-500 (2010).

Koto, T. et al. Eicosapentaenoic acid is anti-inflammatory in preventing choroidal neovascularization in mice. *Invest Ophthalmol Vis Sci* 48, 4328-4334 (2007).

What is claimed:

1. A method of treating age-related macular degeneration comprising:
administering to a patient a therapeutically effective amount of sterculic acid or a pharmaceutically acceptable salt form thereof.

2. The method according to claim 1, wherein the patient is administered a therapeutically effective amount of sterculic acid sufficient to inhibit inflammation induced by 7-ketocholesterol.

3. The method according to claim 1, wherein the patient is administered a therapeutically effective amount of sterculic acid sufficient to inhibit inflammation, cytotoxicity, and/or unregulated angiogenesis induced by 7-ketocholesterol.

4. The method according to claim 1, wherein the patient is administered a therapeutically effective amount of sterculic acid sufficient to inhibit cytotoxicity induced by 7-ketocholesterol.

5. The method according to claim 1, wherein the patient is administered a therapeutically effective amount of sterculic acid sufficient to inhibit unregulated angiogenesis induced by 7-ketocholesterol.

6. The method according to claim 1, wherein the patient is administered a therapeutically effective amount of sterculic acid sufficient to inhibit endothelial cell migration.

7. The method according to claim 1, wherein the age-related macular degeneration is wet age-related macular degeneration.

8. The method according to claim 1, wherein the sterculic acid or pharmaceutically acceptable salt form thereof is administered to the eye of the patient.

9. The method according to claim 1, wherein the sterculic acid or pharmaceutically acceptable salt form thereof is administered one to four times daily.

10. The method according to claim 1, comprising administering a pharmaceutically acceptable salt form of sterculic acid.

* * * * *